(12) United States Patent
Holaday et al.

(10) Patent No.: US 6,413,513 B1
(45) Date of Patent: Jul. 2, 2002

(54) COMPOSITIONS AND METHODS FOR INHIBITING ENDOTHELIAL CELL PROLIFERATION AND REGULATING ANGIOGENESIS USING CANCER MARKERS

(75) Inventors: John W. Holaday, Bethesda; Anne H. Fortier, Rockville, both of MD (US)

(73) Assignee: Entremed, Inc., Rockville, MD (US)

( * ) Notice: Subject to any disclaimer, the term of this patent is extended or adjusted under 35 U.S.C. 154(b) by 0 days.

(21) Appl. No.: 09/413,049

(22) Filed: Oct. 6, 1999

Related U.S. Application Data

(63) Continuation-in-part of application No. 09/316,802, filed on May 21, 1999.
(60) Provisional application No. 60/086,586, filed on May 22, 1998.

(51) Int. Cl.[7] ...................... A61K 39/395; A61K 38/48; A61K 38/00; A61K 38/16
(52) U.S. Cl. ................. 424/138.1; 424/130.1; 424/94.64; 514/2; 514/8
(58) Field of Search .................. 514/2, 8; 530/324; 424/94.1, 138.1, 130.1, 94.64

(56) References Cited

FOREIGN PATENT DOCUMENTS

WO          WO 97/11172           3/1997

OTHER PUBLICATIONS

Algire et al., Vascular reactions of normal and malignant tumors in vivo. I. Vascular reactions of mice to wounds and to normal and neoplastic transplants, J. Natl. Canc. Inst., 1945, pp. 73–85, vol. 6.
Angiolillo, et al., Human interferon–inducible Protein 10 is a poten inhibitor of angiogenesis in vovo, J. Exp. Med., 1995, pp. 441–446, vol. 74.
Brawer et al., "Predictors of Pathologic Stage in Prostatic Carcinoma", Cancer, Feb. 1, 1994, pp. 678–687, vol. 73, No. 3.
Brem et al., "Interstitial chemotherapy with drug polymer implants for the treatment of recurrent gliomas", Neurosurg., Mar. 1991, pp. 441–446, vol. 74.
Cao, et al., "gro–B, a–C–X–C–Chemokine, Is an Angiogenesis Inhibitor That Suppresses the Growth of Lewis Lung Carcinoma in Mice", J. Exp. Med., Dec. 1995, pp. 2069–2077, vol. 182.
Chen, et al., "A Strategy to Discover Circulating Angiogenesis Inhibitors Generated by Human Tumors", Cancer Research, Oct. 1, 1995, pp. 4230–4233, vol. 55.
Clapp, et al., "The 16–Kilodalton N–Terminal Fragment of Human Prolactin is a Potent Inhibitor of Angiogenesis", Endocrinology, Mar. 1993, pp. 1292–1299, vol. 133.
Colman et al (editors), "Hemostasis and Thrombosis", Basic Principles and Clinical Practice Second Edition, 2000 pp. 20 and 21, J.B. Lipincott Company Publishers, Philadelphia.

Dameron et al., "Control of Angiogenesis in Fibroblasts by p53 Regulation of Thrombospondin–1", Science, Sep. 9, 1994, pp. 1582–1584, vol. 265.
Folkman et al, "Long–term culture of capillary endothelial cells", Proc. Natl. Acad. Sci. USA, Oct. 1979, pp. 5217–5221, vol., 76, No. 10.
Folkman, Judah, "Tumor angiogenesis and tissue factor", Nature Medicine, Feb. 1996, pp. 167–168, vol. 2, No. 2.
Folkman, Judah, "What is the Evidence That Tumors Are Angiogenesis Dependent?", Journal of the National Cancer Institute, Jan. 3, 1990, pp. 4–6, vol. 82, No. 1.
Folkman, Judah, "Angiogenesis in cancer, vascular, rheumatoid and other disease", Medicine, 1995, pp. 27–31, vol. 1, No. 1.
Folkman et al., "Induction of angiogenesis during the transition from hyperplasia to neoplasia", Nature, May 4, 1989, pp. 58–61, vol. 399.
Folkman, Judah, "Tumor Angiogenesis: Therapeutic Implications", The New England Journal of Medicine, Nov. 18, 1971, pp. 1182–1186, vol. 285, No. 21.
Gavrieli et al., "Identification of Programmed Cell Death In Situ via Specific Labeling of Nuclear DNA Fragmentation", The Journal of Cell Biology, 1992, pp. 493–501, vol. 119.
Gimbrone et al., "Tumor Growth and Neovascularization: An Experimental Model Using the Rabbit Cornea", Journal of the National Cancer Institute, Feb. 1974, pp. 413–427, vol. 52, No. 2.
Good et al., "A tumor suppressor–dependent inhibitor of angiogenesis is immunologically and functionally indistinguishable from a fragment of thrombospondin", Proc. Natl. Acad. Sci. USA, Sep. 1990, pp. 6624–6628, vol. 87.
Grant et al., "Two Different Laminin Domains Mediate the Differentiation of Human Endothelial Cells into Capillary–like Structures in Vitro", Cell, Sep. 8, 1989, vol. 58.
Gross et al., "Increased capillary endothelial cell protease activity in response to angiogenic stimuli in vitro", Proc. Natl. Acad. Sci. USA, May 1983, pp. 2623–2627, vol. 80.
Gupta et al., "A potent inhibitor of endothelial cell proliferation is generated by proteolytic cleavage of the chemokine platelet factor 4", Proc. Natl. Acad. Sci. USA, Aug. 1995, pp. 7799–7803, vol. 92.

(List continued on next page.)

*Primary Examiner*—Yvonne Eyler
*Assistant Examiner*—Janet L. Andres
(74) *Attorney, Agent, or Firm*—Kilpatrick Stockton LLP

(57) ABSTRACT

Compositions and methods for regulating angiogenic activity wherein the compositions comprise cancer markers including kallikreins such as prostate-specific antigen (PSA), serine protease homologs, or active fragments thereof are provided. Serine proteases and kallikreins exhibit potent antiangiogenic activity on human and other animal cells, particularly endothelial cells. More particularly, PSA, PSA homologs, and inhibitory fragments thereof may be combined with a pharmaceutically acceptable excipient or carrier and used to inhibit angiogenesis and angiogenesis-related diseases such as cancer, arthritis, macular degeneration, and diabetic retinopathy.

6 Claims, 7 Drawing Sheets

OTHER PUBLICATIONS

Hanlon et al., "Modeling Postradiation Prostate Specific Antigen Level Kinetics", Cancer, Jul. 1, 1998, pp. 130–134, vol. 83, No. 1.

Hodge et al., "A Recombinant Vaccinia Virus Expressing Human Prostate–Specific Antigen (PSA): Safety and Immunogenicity in a Non–Human Primate", Int. J. Cancer, 1995, pp. 231–237, vol. 63.

Holmgren et al., "Dormancy of micrometastases: Balanced proliferation and apoptosis in the presence of angiogenesis suppression", Nature Medicince, Feb. 1995, pp. 149–153, vol. 1, No. 2.

Homandberg et al., "Heparin–Binding Fragments of Fibronectin are Potent Inhibitors of Endothelial Cell Growth", Am. J. Path., Sep. 1985, pp. 327–332, vol. 120, No. 3.

Hori et al., "Suppression of Solid Tumor Growth by Immunoneutralizing Monoclonal Antibody against Human Basic Fibrblast Growth Factor", Cancer Research, Nov. 15, 1991, pp. 6180–6184, vol. 51.

Kandel et al., "Neovascularization Is Associated with a Switched to the Export of bFGF in the Multistep Development of Fibrosarcoma", Cell, Sep. 20, 1991, pp. 1095–1114, vol. 66.

Kim et al., "Inhibition of vascular endothelial growth factor–induced angiogenesis suppresses tumor growth in vivo", Nature, Apr. 29, 1993, pp. 841–8444, vol. 362.

Kim et al., "Molecular and immunological analysis of genetic prostate specific antigen (PSA) vaccine", Oncogene, 1998, pp. 3125–3135, vol. 17.

Lilja et al., "Prostate–Specific Antigen in Serum Occurs Predominantly in Complex with α1–Antichymotrypsin", Clin. Chem., 1991, pp. 1618–1625, vol. 37, No. 9.

Maione et al., "Inhibition of Angiogenesis by Recombinant Human Platelet Factor–4 and Related Peptides", Science, 1990, pp. 77–79, vol. 247.

Millauer et al., "Glioblastoma growth inhibited in vivo by a dominant–negative Flk–1 mutant", Nature, Feb. 10, 1994, pp. 576–579, vol. 367.

Muragaki et al., "Mouse Col18a1 is expressed in a tissue–specific manner as three alternative variants and is localized in basement membrane zones", Proc. Natl. Acad. Sci. USA, Sep. 1995, pp. 8763–8767, vol. 92.

Nelson et al., "Murine Epidermal Growth Factor (EGF) Fragment (33–43) Inhibits Both EGF– and Laminin– dependent Endothelial Cell Motility and Angiogenesis", Cancer Research, Sep. 1, 1995, pp. 3772–3776, vol. 55.

Nguyen et al., "Quantitation of Angiogenesis and Antiangiogenesis in the Chick Embryo Chorioallantoic Membrane", Microvascular Research, 1994, pp. 31–40, vol. 47.

O'Reilly et al., "Endogeneous Inhibitors of Angiogenesis", Proceedings of the American Assoc. for Cancer Research, Mar. 1996, p. 669, vol. 37 (Abstract only).

O'Reilly et al., "Angiostatin induces and sustains dormancy of human primary tumors in mice", Nature Medicine, Jun. 1996, pp. 689–691, vol. 2, No. 6.

O'Reilly et al., "The Suppression of Tumor Metastases by a Primary Tumor", Surigcal Forum, 1993, pp. 474–475, vol. XLIV.

O'Reilly et al., "Angiostatin: A Novel Angiogenesis Inhibitor That Mediates the Suppression of Metastases by a Lewis Lung Caricnoma", Cell, Oct. 21, 1994, pp. 315–328, vol. 79.

O'Reilly et al., "Angiostatin: A Circulating Endothelial Cell Inhibitor That Suppresses Angiogenesis and Tumor Growth", Cold Spring Harbor Symposia on Quantitative Biology, 1994, pp., 471–482, vol. LIX.

Obeso et al., "Methods in Laboratory Investigation–A Hemangioendothelioma–Derived Cell Line: Its Use as a Model for the Study of Endothelial Cell Biology", Laboratory Investigation, 1990, pp. 259–269, vol. 63, No. 2.

Oh et al., "Isolation and sequencing of cDNAs for proteins with multiple domains of Gly–Xaa–Yaa repeats identify a distinct family of collagenous proteins", Proc. Natl. Acad. Sci. USA, May 1994, pp. 4229–4233, vol. 91.

Parangi et al., "Antiangiogenic therapy of transgenic mice impairs de novo tumor growth", Proc. Natl. Acad. Sci. USA, Mar. 1996, pp. 2002–2007, vol. 93.

Rastinejad et al., "Regulation of the Activity of a New Inhibitor of Angiogenesis by a Cancer Suppressor Gene", Cell, Feb. 10, 1989, pp. 345–355, vol. 56.

Rehn et al., "Identification of Three N–terminal Ends of Type XVII Collagen Chains and Tissue–specific Differences in the Expression of the Corresponding Transcripts", The Journal of Biological Chemistry, 1995, pp. 4705–4711, vol. 270, No. 9.

Rehn et al., "α1(XVIII), a collagen chain with frequent interruptions in the collagenous sequence, a distinct tissue distribution, and homology with type XV collagen", Proc. Natl. Acad. Sci. USA, May 1994, pp. 4234–3238, vol. 91.

Riegman et al., "Characterization of the Human Kallikrein Locus", Genomics, 1992, pp. 6–11, vol. 14.

Robbins, Kenneth, "The Plasminogen–Plasmin Enzyme System", Fibrinolysis, 1987, pp. 340–357.

Sage et al., "Inhibition of Endothelial Cell Proliferation by SPARC is Mediated Through a $Ca^{2+}$ –Binding EF–Hand Sequence", Journal of Cellular Biochem., 1995, pp. 127–140, vol. 57.

Sakamoto et al., "Inhibition of Angiogenesis and Tumor Growth by a Synthetic Laminin Peptide, CFPGYIG-SR–$NH_2$", Cancer Research, Feb. 1, 1991, pp. 903–906, vol. 51.

Sambrook et al, editors, "Molecular Cloning—A Laboratory Manual Second Edition", Cold Spring Harbor Laboratory Press, 1989, pp. 17.37–17.41.

Shackelford et al., "Biochemical properties and cellular effects of prostate specific antigen", Proceedings of the American Association for Cancer Research, Mar. 1997, p. 428, vol. 38 (abstract only).

Sokoll et al., "Prostate–Specific Antigen– It's Discovery and Biochemical Characterisitcs", Urologic Clinics of NorthAmerica, May 1997, pp. 253–259, vol. 24, No. 2.

Strieter et al., "Interferon γ–inducible Protein 10(IP–10), A Member of the C–X–C Chemokine Family, Is An Inhibitor of Angiogenesis", Biochemical and Biophysical Research Communications, May 5, 1995, pp. 51–57, vol. 210, No. 1.

Studier et al., "Use of T7 RNA Polymerase to Direct Expression of Cloned Genes", Methods in Enzymology, 1990, pp. 60–89, vol. 185.

Teicher et al., "Potentiation of Cytotoxic Cancer Therapies by TNP–740 Alone and With Other Anti–Angiogenic Agents", Int. J. Cancer, 1994, pp. 920–925, vol. 57.

Tolsma et al., "Peptides Derived from Two–Separate Domains of the Matrix Protein Thrombospondin–1 Have Anti–Angiogenic Activity", The Journal of Cell Biology, Jul. 1993, pp. 497–511, vol. 122, No. 2.

Voest et al., "Inhibition of Angiogenesis In Vivo by Interleukin 12", Journal of the National Cancer Institute, Apr. 19, 1995, pp. 581–586, vol. 87, No., 8.

Wakui et al., "Tumour Angiogenesis in Prostatic Carcinoma with and without Bone Marrow Metastasis: A Morphometric Study", Journal of Pathology, 1992, pp. 257–262, vol. 168.

Weidner et al., "Tumor Angiogenesis Correlates with Metastasis in Invasive Prostate Carcinoma", American Journal of Pathology, Aug. 1993, pp. 401–409, vol. 143, No. 2.

Weidner et al., "Tumor Angiogenesis and Metastasis—Correlation in Invasive Breast Carcinoma", The New England Journal of Medicine, Jan. 3, 1991, pp. 1–8, vol. 324, No. 1.

Yang, Ning–Sun, "Gene Transfer into Mammalian Somatic Cells In Vivo", Critical Reviews in Biochemistry, 1992, pp. 335–356, vol. 12, No. 4.

Folkman, "Angiogenesis and its Inhibitors", Important Advances In Oncology, J.B. Lippencott Company, 1985.

O'Reilly et al., "Endostatin: An endogenous inhibitor of angiogenesis and tumor growth", Cell, Jan. 24, 1997, pp. 277–285, vol. 88, No. 2 (Abstract only).

Cohen et al., "Biological effects of prostate specific antigen as an insulin–like growth factor bindinprotein–3 protease", Journal of Endocrinology, 1994, pp. 407–415, vol. 142.

Beckner, M., Factors Promoting Tumor Angiogenesis, 1999, Cancer Investigations, vol. 17, pp. 594–623.*

Gill et al., N. Eng. J. Med. 335:1261, 1996.*

Mukhopadyay et al., Cancer Res., 55:6161, 1995.*

Takigawa et al., Cancer Lett. 50:4131, 1990.*

* cited by examiner

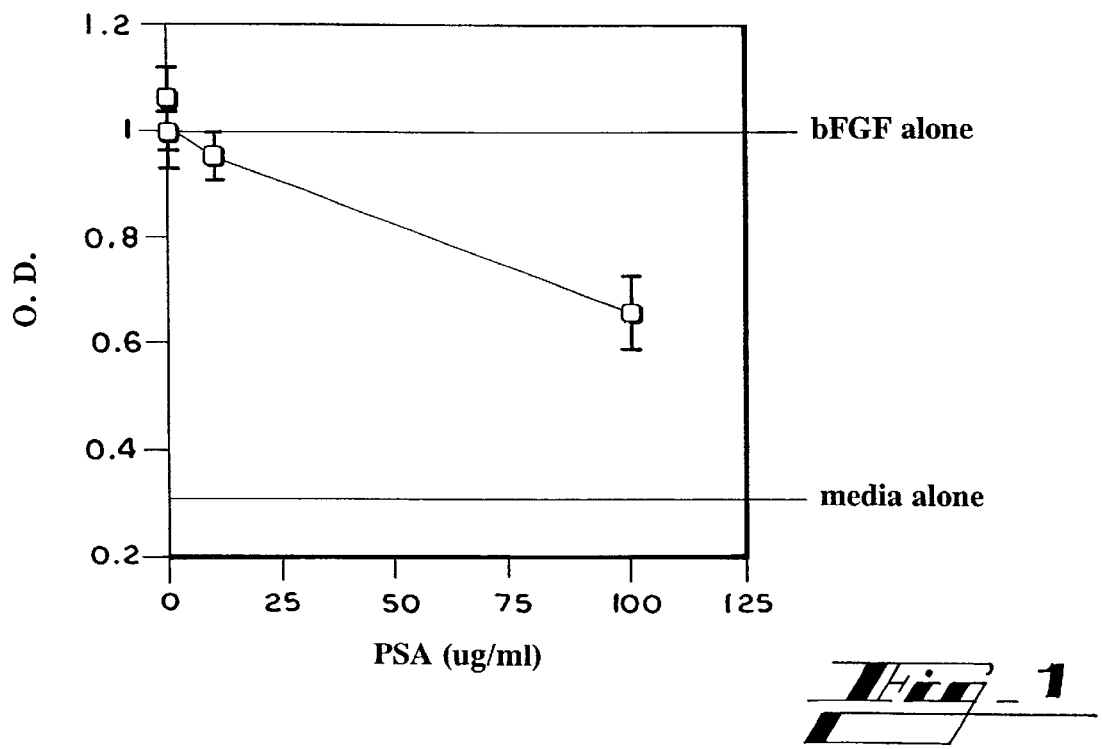
Fig_1
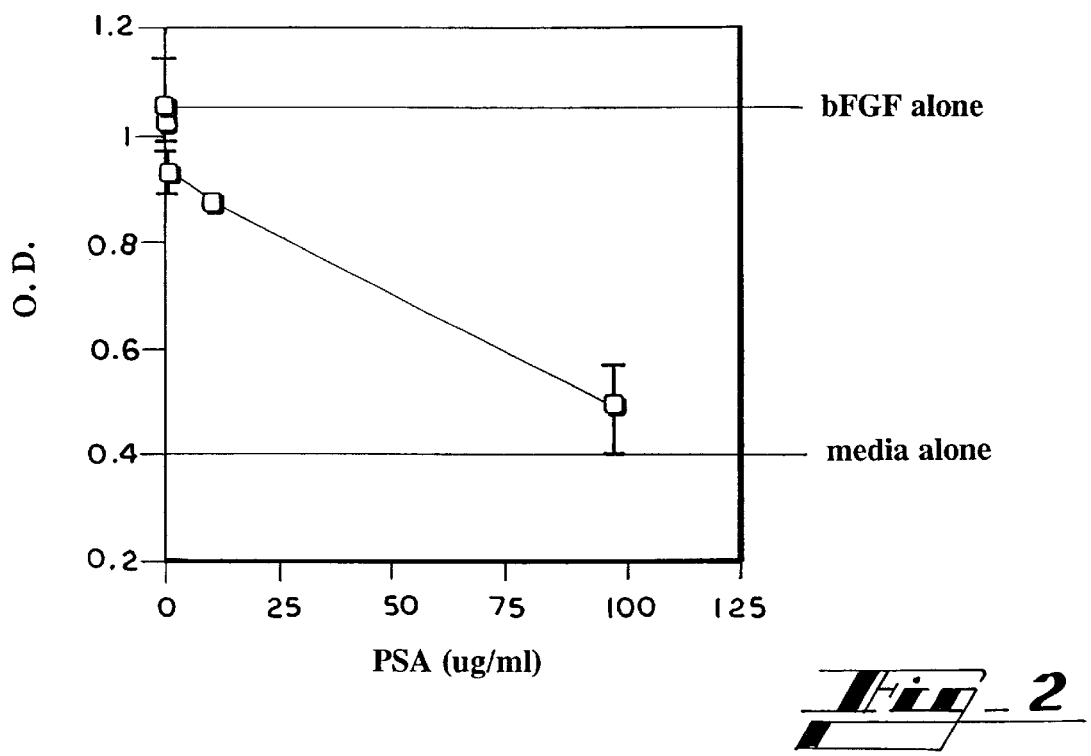
Fig_2

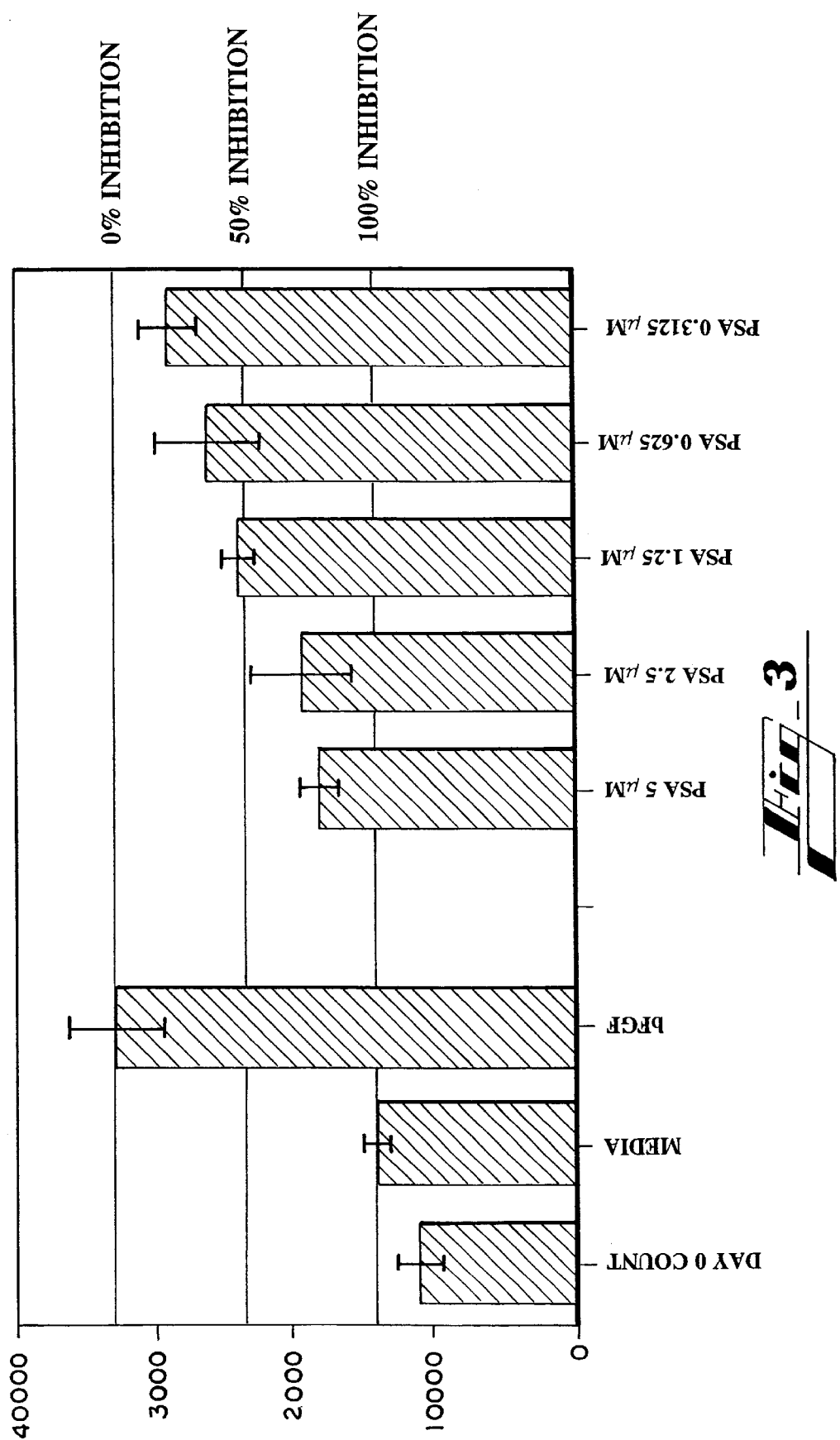

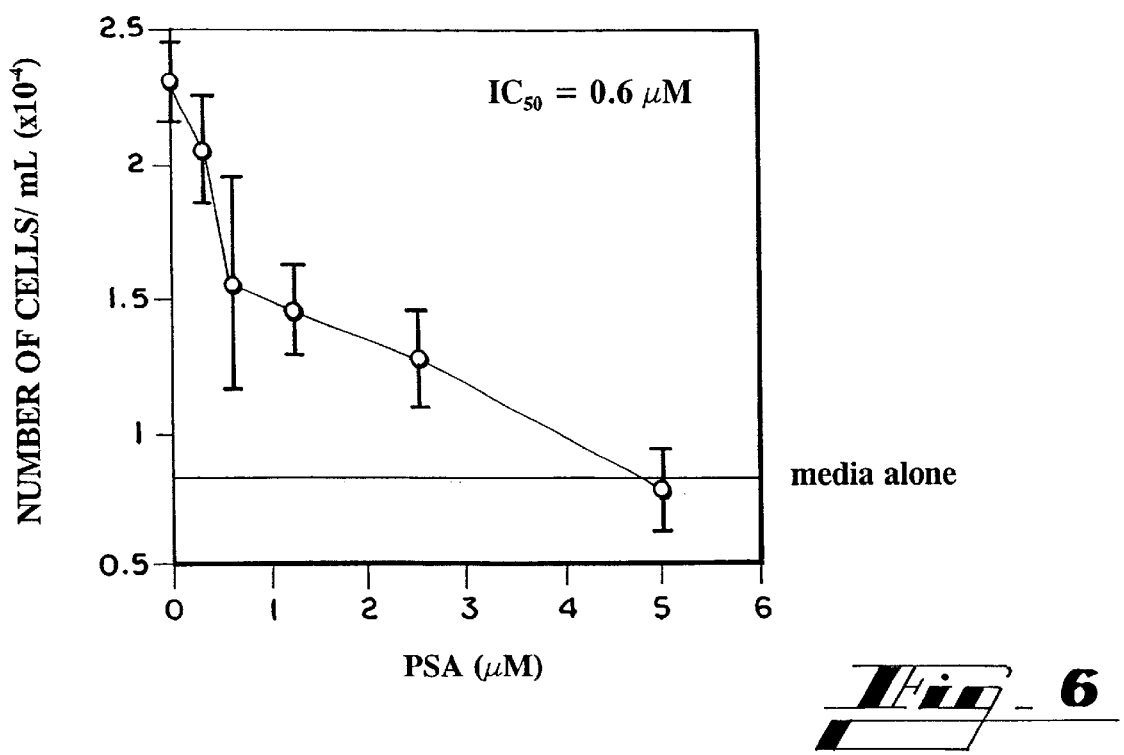
Fig_6
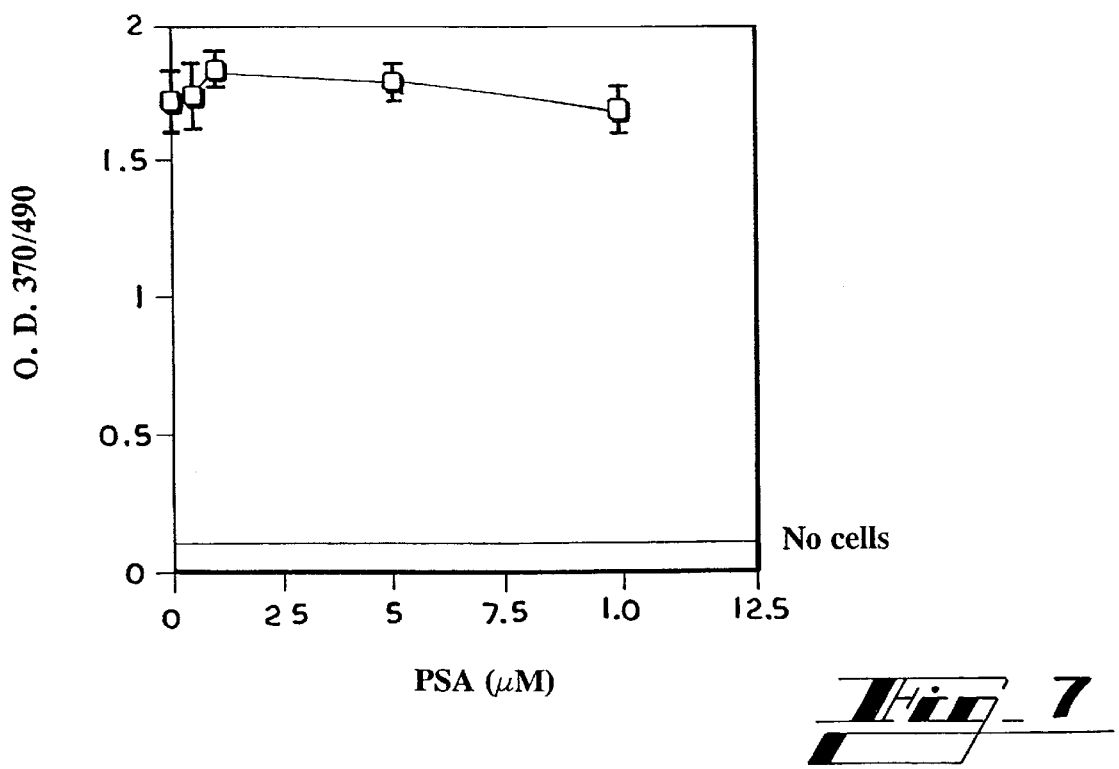
Fig_7

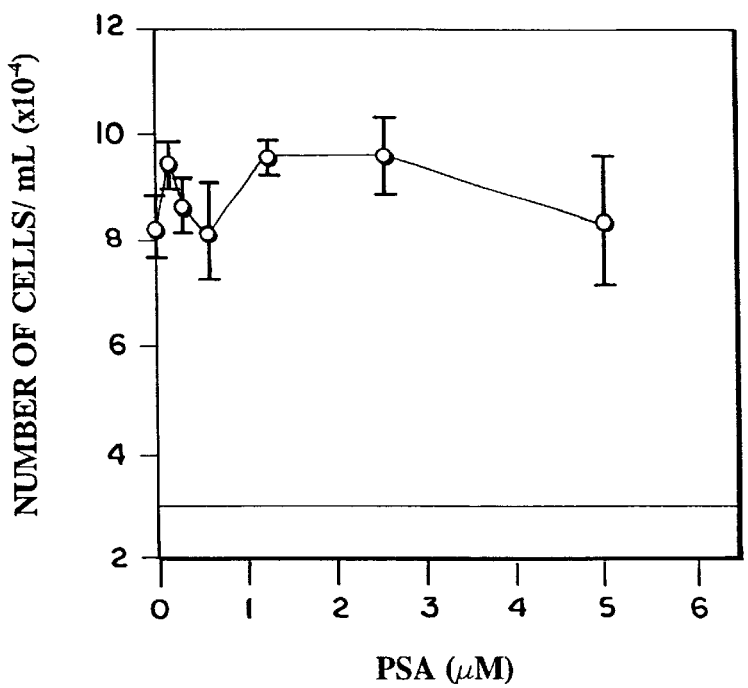
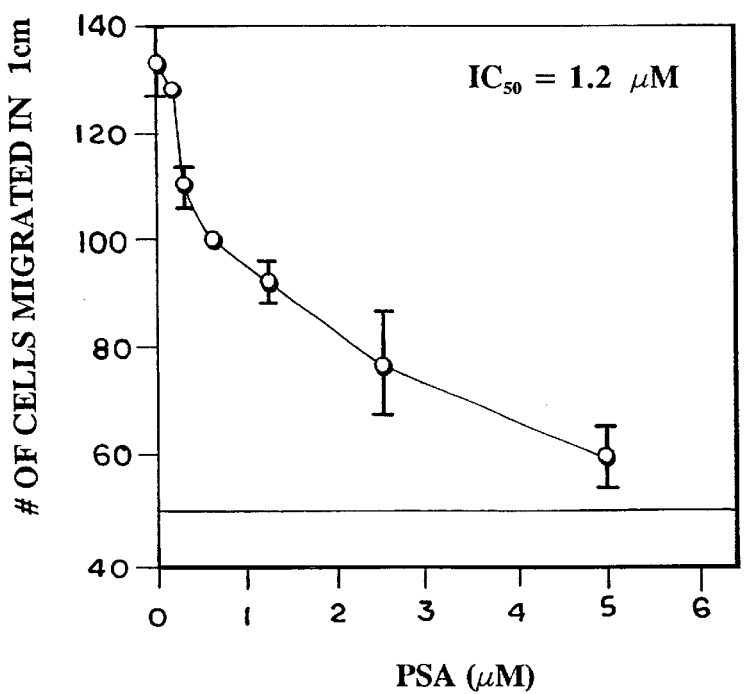

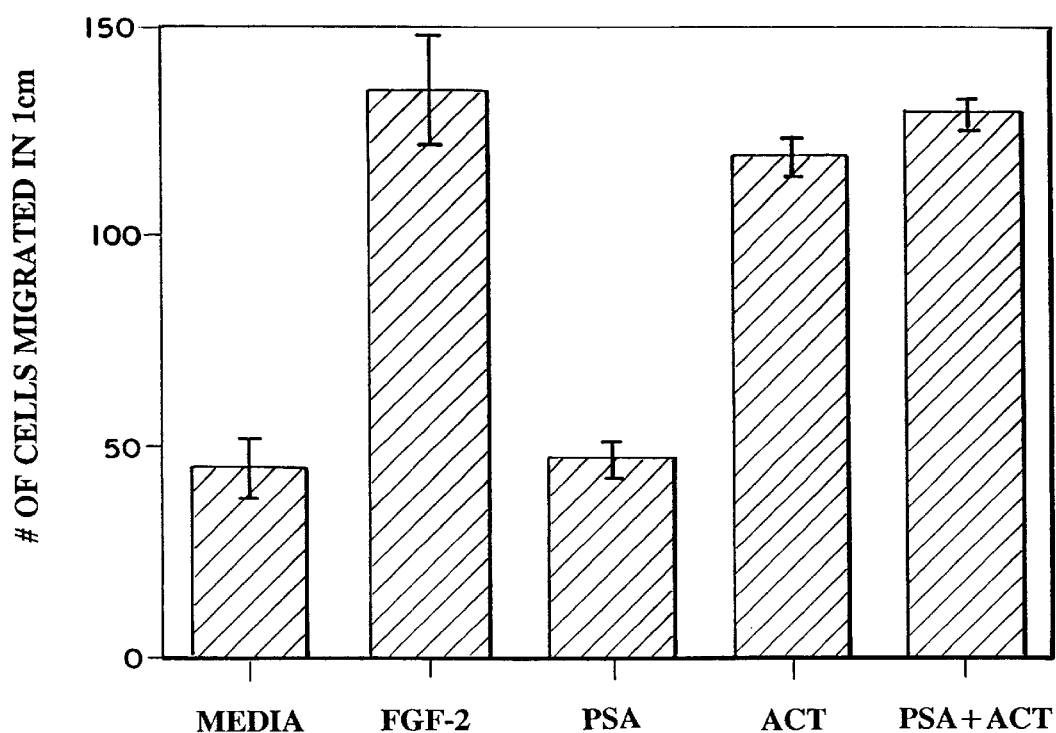
_Fig_12

COMPOSITIONS AND METHODS FOR INHIBITING ENDOTHELIAL CELL PROLIFERATION AND REGULATING ANGIOGENESIS USING CANCER MARKERS

CROSS-REFERENCE TO RELATED PATENT APPLICATIONS

This application is a C-I-P of to U.S. patent application Ser. No. 09/316,802 filed May 21, 1999 which claims priority to U.S. Provisional Application Ser. No. 60/086,586 filed on May 22, 1998, both of which are incorporated herein in its entirety.

TECHNICAL FIELD

This application relates to a novel use of cancer markers such as kallikreins, including prostate-specific antigen (PSA), as inhibitors of angiogenesis useful for treating angiogenesis-related diseases such as angiogenesis-dependent cancer. The invention further relates to novel compositions and methods for curing angiogenesis-dependent cancer. In addition, the present invention relates to molecular probes for monitoring biosynthesis, to antibodies that are specific for serine proteases including kallikreins, to the development of peptide agonists and antagonists to kallikrein receptors, and to cytotoxic agents linked to kallikrein peptides.

BACKGROUND OF THE INVENTION

Cancer Markers

The discovery of cancer markers and tumor markers has significantly enhanced not only diagnosis of cancer but has also contributed to the monitoring of cancer patients for assessing disease progression. A rise in cancer markers is a yardstick with which benign diseases can be distinguished from metastatic disease and also used to evaluate the efficacy of treatments. A decline in cancer markers is often a predictor of possible residual disease if the timing of blood sampling is soon after therapy. Numerous cancer markers are known in the art and are utilized in detection assays such as immunoassays depending upon the intrinsic characteristics of each marker (antigen specificity, molecular heterogeneity) and individual factors (nonspecific increases and renal and hepatic diseases).

Kallikrein

Kallikrein and kallikrein-like enzymes belong to a multigene family of serine proteases present in tissues and body fluids of numerous animals such as mammals and reptiles (i.e. snake venom). Included in the kallikrein family is hk1, a pancreatic/renal kallikrein; hk2, a human glandular kallikrein present in seminal fluid, a protease that activates urokinase type plasminogen activator; and prostate-specific antigen (hk3), a single-chain glycoprotein found in prostate tissue. Pre-kallikrein is converted by limited proteolysis into an active serine protease, and is one of the five major proteins involved in the activation and inhibition of surface mediated pathways in blood clotting. Pre-kallikrein is an important component of the biochemical junctures of intrinsic coagulation with other plasma proteolytic pathways required in the initiation, amplification, and propagation of surface-mediated defense reactions wherein various proteins such as bradykinin are involved. Thus, the molecular events of the contact phase of coagulation activation and inhibition involve pre-kallikrein and the plasma biochemical systems. (Colman et al. 1987).

Plasma kallikrein circulates in the blood as the precursor "pre-kallikrein." Plasma pre-kallikrein is synthesized in the liver and secreted into plasma. However, only 25% of the protein exists as free pre-kallikrein and approximately 75% circulates bound to high molecular weight kininogen (HMWK). The molecular weight of human plasma pre-kallikrein, as assessed by gel filtration, is approximately 100,000 Daltons. By SDS polyacrylamide gel electrophoresis, plasma pre-kallikrein consists of two components having molecular weight 85,000 Daltons and 88,000 Daltons, depending whether the sample has undergone reduction. In plasma, the concentration of pre-kallikrein is estimated to be 35 $\mu$g to 50 $\mu$g/ml.

Following proteolysis, pre-kallikrein is activated to kallikrein and current studies do not demonstrate any clear cut difference in physiochemical or immunochemical properties of zymogen pre-kallikrein, and active enzyme kallikrein in the absence of reduction. Hageman factor (also known as Factor $XII_a$), and Hageman factor fragment (also known as Factor $XII_f$), are both able to convert pre-kallikrein to kallikrein. Unlike pre-kallikrein on reduced SDS gel electrophoresis, kallikrein has two types of subunits: a heavy chain with a molecular weight of approximately 52,000 Daltons, and two light chain variants with a molecular weight of approximately 36,000 Daltons and 33,000 Daltons. Pre-kallikrein circulates mostly complexed to high molecular weight kininogen HMWK, and it is thought that this complex may have protective functions for the pre-kallikrein. Following activation from pre-kallikrein to kallikrein, HMWK is cleaved to release bradykinin. Bradykinin is one of the most potent vasodilators known. (Colman et al. p.254).

The gene for plasma pre-kallikrein has not been isolated or characterized thus far. The messenger RNA for plasma pre-kallikrein, however has been characterized as a cDNA and shown to be approximately 2,300 nucleotides in length. It codes for a leader sequence of 19 amino acids and a mature polypeptide chain of 619 amino acids. The latter peptide in plasma pre-kallikrein is one amino acid longer than that in Factor XI. The activation reaction of pre-kallikrein to kallikrein is due to the cleavage of the peptide bond following arginine 371. Plasma kallikrein is generated as an enzyme composed of a heavy chain (371 amino acids) and a light chain (248 amino acids), held together by a disulfide bond. The catalytic domain or light chain of plasma kallikrein, contains three important amino acids (His-44, Asp-93 and Ser-188) that are directly involved in catalysis. In addition, plasma kallikrein contains 5 N-linked carbohydrate chains as established by amino acid sequence analysis.

The proteins and enzymes of the clotting cascade may perform multiple functions, for example, Factor $XII_a$ may cleave pre-kallikrein to kallikrein, and Factor XI to $XI_a$. Kallikrein can initiate reciprocal activation, generating additional Factor $XII_a$ from Factor XII. Plasma kallikrein leads to the conversion of plasminogen to plasmin and Factor $XII_a$ also converts plasminogen to plasmin. Kallikrein cleavage of HMWK results in the release bradykinin and may also elevate blood pressure by directly converting pro-renin to renin.

Alteration of any of the components of the vascular system, namely vessel cell wall, plasma proteins and platelets can result in an angiogenic disorder. There appear to be two major mechanisms under which the multiple inciting etiologies can be catagorized: endothelial injury and tissue injury. Endothelial injury relates to disease states such as infections that specifically injure the endothelium, with resultant kallikrein-kinin activation.

Injury to the vascular endothelium, such as occurs in endotoxemia, exposes basement membrane. Consequently collagen, along or in combination with proteoglycans or other components, activates Factor XII. Following Factor XII activation, intrinsic coagulation, activation of fibrinolysis and kinin formation occur. (Colman et al. p. 976).

Patients with bacterial infections, especially those caused by gram negative bacteria, may have elevated levels of plasma kallikrein. The hypotensive effect of kallikrein may contribute to the development of disseminated intravascular coagulation by reducing blood flow to reticuloendothelial organs thereby impairing clearance of activated coagulation factors.

Prostate-Specific Antigen

One important member of the kallikrein family is prostate-specific antigen. (Riegman et al.) The prostate-specific antigen (PSA) molecule is a single-chain glycoprotein consisting of approximately 237 amino acids and has a molecular weight of 28,430 daltons as determined by ion-spray mass spectroscopy. (Sokoll et al. 1997). The gene for PSA is located on the long arm of chromosome 19 and is approximately 6 kilobases in size, consisting of 4 introns and 5 exons. The PSA gene is under androgen regulation as evidenced by an androgen-responsive element in the promoter region. PSA is thought to be translated as a 261 amino acid prepropeptide. Although not isolated, the 244 propeptide zymogen form of PSA results after cleavage of the leader peptide during translation. The 237 amino acid active enzyme then is surmised to result from subsequent cleavage with as yet unidentified proteases. Structurally, the molecule is thought to possess five disulfide bonds owing to the presence of 10 cysteine residues with the active site of the enzyme composed of three amino acids, histidine 41, aspartate 96 and serine 189.

PSA is synthesized in the ductal epithelium and prostatic acini and located within the cell in cytoplasmic granules and vesicles, rough endoplasmic reticulum, vacuoles and secretory granules, and lysosmal dense bodies. PSA is found in normal hyperplastic, primary, and metatstatic prostate tissue. PSA is secreted into the lumina of the prostatic ducts via exocytosis to become a component of seminal plasma and reaches serum after diffusion from luminal cells through the epithelial basement membrane and prostatic stroma, where it can pass through the capillary basement membrane and epithelial cells or into the lymphatics. (Sokoll et al. 1997).

Despite original assumptions that PSA was a tissue-specific and gender-specific antigen, immunohistochemical and immunoassay methods have detected PSA in female and male periurethral glands, anal glands, apocrine sweat glands, apocrine breast cancers, salivary gland neoplasms, and most recently in human breast milk.

PSA functions as a serine protease exhibiting proteolytic activity similar to chymotrypsin, cleaving peptide bonds carboxy terminus of certain leucine and tyrosine residues. Based on its function, amino-acid structure and gene location, PSA is recognized as a member of the human kallikrein family.

In males, PSA is secreted from the lumen of the prostate and enters the seminal fluid as it passes through the prostate. In the seminal fluid are gel-forming proteins, primarily semenogelin I and II and fibronectin, which are produced in the seminal vesicles. These proteins are the major constituents of the seminal coagulum that forms at ejaculation and functions to entrap spermatozoa. PSA functions to liquefy the coagulum and break down the seminal clot through proteolysis of the gel-forming proteins into smaller more soluble fragments, thus releasing the spermatozoa. PSA also may modulate cell growth factor (IGF) binding protein 3, resulting in decreased binding with IGF-1, thus promoting cell growth. (Sokoll et al. 1997).

As it is used hereinafter, the term "PSA" refers to PSA as described above, peptide fragments of PSA that have angiogenesis inhibiting activity, and analogs of PSA that have substantial sequence homology (as defined herein) to the amino acid sequence of PSA, which have angiogenesis inhibiting activity.

Angiogenesis and Cancer

Several lines of direct evidence now suggest that angiogenesis is essential for the growth and persistence of solid tumors and their metastases (Folkman, 1989; Hori et al., 1991; Kim et al., 1993; Millauer et al., 1994). To stimulate angiogenesis, tumors upregulate their production of a variety of angiogenic factors, including the fibroblast growth factors (FGF and bFGF) (Kandel et al., 1991) and vascular endothelial cell growth factor/vascular permeability factor (VEGF/VPF). However, many malignant tumors also generate inhibitors of angiogenesis, including ANGIOSTATIN® protein and thrombospondin. (Chen et al., 1995; Good et al., 1990; O'Reilly et al., 1994). It is postulated that the angiogenic phenotype is the result of a net balance between these positive and negative regulators of neovascularization. (Good et al., 1990; O'Reilly et al., 1994; Parangi et al., 1996; Rastinejad et al., 1989). Several other endogenous inhibitors of angiogenesis have been identified, although not all are associated with the presence of a tumor. These include, platelet factor 4 (Gupta et al., 1995; Maione et al., 1990), interferon-alpha, interferon-inducible protein 10 (Angiolillo et al., 1995; Strieter et al., 1995), which is induced by interleukin-12 and/or interferon-gamma (Voest et al., 1995), gro-beta (Cao et al., 1995), and the 16 kDa N-terminal fragment of prolactin (Clapp et al., 1993).

One example of an angiogenesis inhibitor that specifically inhibits endothelial cell proliferation is ANGIOSTATIN® protein. (O'Reilly et al., 1994). ANGIOSTATIN® protein is an approximately 38 kiloDalton (kDa) specific inhibitor of endothelial cell proliferation. ANGIOSTATIN® protein is an internal fragment of plasminogen containing at least three of the five kringles of plasminogen ANGIOSTATIN® protein has been shown to reduce tumor weight and to inhibit metastasis in certain tumor models. (O'Reilly et al., 1994). Another angiogenesis inhibitor is ENDOSTATIN® protein, which is a carboxy fragment of collagen XV or XVIII. (O'Reilly et al., 1997).

What is needed is the discovery and development of additional anti-angiogenic agents that may be used alone or in combination with known angiogenic agents in order to treat cancer and hyperproliferative disorders.

SUMMARY OF THE INVENTION

The present invention generally relates to cancer markers including kallikreins and specifically to prostate-specific antigen (PSA) as angiogenesis inhibitors and methods of use thereof. PSA is a potent and specific inhibitor of endothelial cell function and angiogenesis. Systemic therapy with kallikreins such as PSA, causes suppression of tumor-induced angiogenesis, and exhibits strong antitumor activity.

PSA has a molecular weight of approximately 28,430 Daltons as determined by ion-spray mass spectroscopy and is capable of inhibiting endothelial cell function in cultured endothelial cells.

The present invention provides methods and compositions for treating diseases and processes mediated by undesired and uncontrolled angiogenesis by administering to a human or animal with the undesired angiogenesis a composition comprising serine proteases including kallikreins such as purified PSA, or PSA derivatives, in a dosage sufficient to inhibit angiogenesis. The present invention is particularly useful for treating or for repressing the growth of tumors. Administration of PSA to a human or animal with metastasized tumors prevents the growth or expansion of those tumors. The invention further provides methods and compositions for regulating endothelial cell function in vivo as well as in vitro.

The present invention also includes kallikrein peptide fragments that can be labeled isotopically or with other molecules or proteins for use in the detection and visualization of kallikrein binding sites with state of the art techniques, including, but not limited to, positron emission tomography, autoradiography, flow cytometry, radioreceptor binding assays, and immunohistochemistry.

The present invention also includes PSA, PSA fragments, or PSA receptor agonists and antagonists linked to cytotoxic agents for therapeutic and research applications.

In addition, PSA peptides may act as agonists and antagonists of the PSA receptor, thereby enhancing or blocking the biological activity of PSA. Such peptides are used in the isolation of the PSA receptor.

A surprising discovery is that various forms of serine proteases including recombinant kallikreins, such as recombinant PSA proteins, can serve as sustained release anti-angiogenesis compounds when administered to a tumor-bearing animal.

The present invention also relates to methods of using PSA protein and peptide fragments, corresponding nucleic acid sequences, and antibodies that bind specifically to the inhibitor and its peptides, to diagnose endothelial cell-related diseases and disorders.

The invention further encompasses a method for identifying receptors specific for PSA, and the receptor molecules identified and isolated thereby.

An important medical method is a new form of birth control, wherein an effective amount of kallikrein (for example PSA) is administered to a female such that uterine endometrial vascularization is inhibited and embryo implantation cannot occur or be sustained.

A particularly important aspect of the present invention is the discovery of a novel and effective method for treating angiogenesis-related diseases, particularly angiogenesis-dependent cancer, in patients, and for curing angiogenesis-dependent cancer in patients. The method unexpectedly provides the medically important result of inhibition of tumor growth and reduction of tumor mass. The method relates to the co-administration of a serine protease or kallikrein of the present invention and another anti-angiogenesis compound, such as ENDOSTATIN® protein or ANGIOSTATIN® protein. Accordingly, the present invention also includes formulations containing PSA, ENDOSTATIN® protein, and/or ANGIOSTATIN® protein, which are effective for treating or curing angiogenesis-dependent diseases.

Accordingly, it is an object of the present invention to provide compositions and methods comprising serine proteases including kallikreins useful for the treatment of angiogenic disorders.

Another object of the present invention is to provide compositions and methods comprising prostate-specific antigen useful for the treatment of angiogenic disorders.

It is another object of the present invention to provide compositions and methods of treating diseases and processes that are mediated by angiogenesis.

It is yet another object of the present invention to provide compositions and methods for treating diseases and processes that are mediated by angiogenesis including, but not limited to, hemangioma, solid tumors, leukemia, metastasis, telangiectasia psoriasis scleroderma, pyogenic granuloma, myocardial angiogenesis, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, surgical adhesions, peptic ulcer, fractures, keloids, vasculogenesis, hematopoiesis, ovulation, menstruation, and placentation.

It is another object of the present invention to provide compositions and methods for treating or repressing the growth of a cancer.

Still another object of the present invention is to provide compositions and methods consisting of antibodies to PSA that are selective for specific regions of the PSA molecule.

It is another object of the present invention to provide compositions and methods for the detection or prognosis of anti-angiogenesis activity.

It is yet another object of the present invention to provide a therapy for cancer that has minimal side effects.

Still another object of the present invention is to provide compositions comprising PSA or PSA peptide linked to a cytotoxic agent for treating or repressing the growth of a cancer.

These and other objects, features and advantages of the present invention will become apparent after a review of the following detailed description of the disclosed embodiments and the appended claims.

BRIEF DESCRIPTION OF THE FIGURES

FIG. 1 is a dose response graph showing inhibition of proliferation activity in bFGF stimulated human umbilical vein endothelial cells following administration of PSA.

FIG. 2 is a dose response graph showing inhibition of proliferation activity in bFGF stimulated human umbilical vein endothelial cells following administration of PSA.

FIG. 3 is a graph showing inhibition of proliferation activity in bFGF stimulated bovine capillary endothelial cells following administration of PSA.

FIG. 6 is a graph showing the effects of PSA on proliferation of human microvascular dermal cells (HMVEC-d) in vitro.

FIG. 7 is a graph showing the effects of PSA on proliferation of murine melanoma B16BL6 cells (tumor cell lines).

FIG. 8 is a graph showing the effects of PSA on proliferation of human prostate carcinoma (PC3).

FIG. 9 is a graph showing the effects of PSA on migration of FGF-2-stimulated HUVECs.

FIG. 12 is a graph showing HUVEC migration inhibitory activity of PSA as assessed in the presence or absence of ACT. For comparison, number of cells that migrated in response to media alone and FGF-2 is shown. Active PSA was preincubated with an equimolar concentration of ACT.

DETAILED DESCRIPTION OF THE INVENTION

Figure 4:
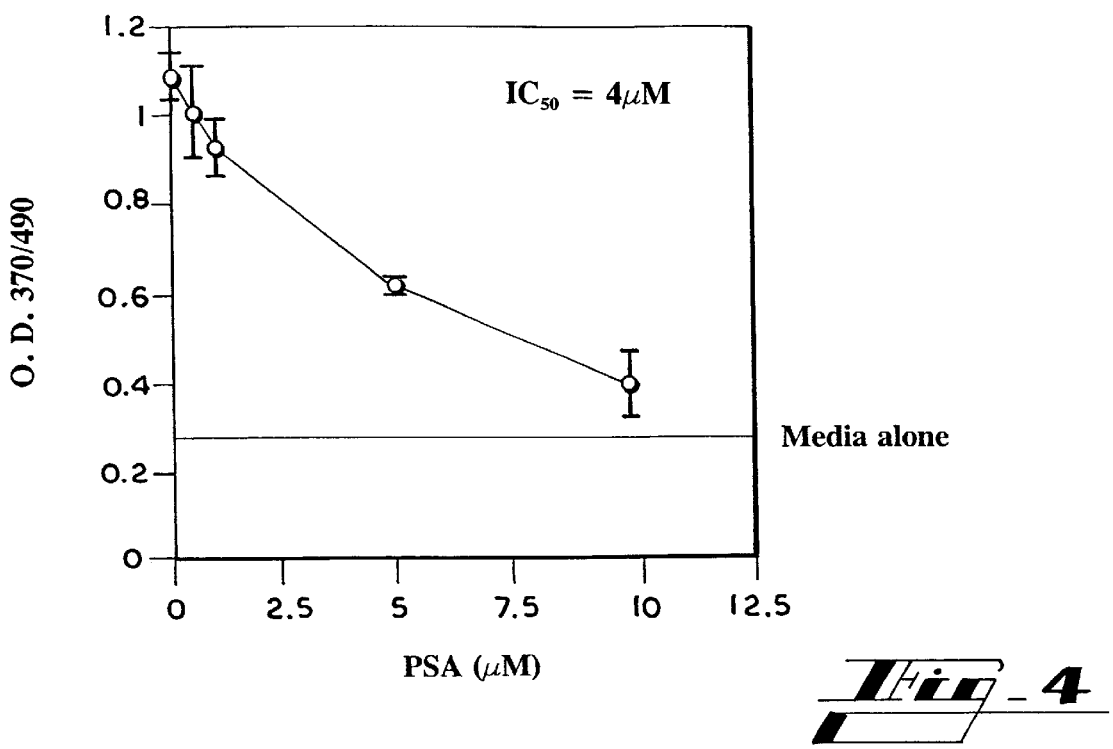
FIG. 4 is a graph showing the effects of PSA on proliferation of human umbilical vein endothelial cells (HUVEC) in vitro.

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein are hereby incorporated in their entireties by reference, including cancer U.S. patent application Ser. No. 09/316,802 filed May 21, 1999, and U.S. Provisional Patent Application Ser. No. 60/086,586 filed May 22, 1998.

Applicants have discovered a novel property for a class of protein molecules. These protein molecules are generally known as cancer markers, they include kallikreins and have the surprising ability to regulate angiogenic function when added to proliferating endothelial cells. "Prostate-Specific Antigen" (PSA) is a protein belonging to the family of kallikreins and as used herein, it is to be understood that the term PSA includes PSA analogs, homologs and active peptides thereof.

The term "cancer markers" refers to biomolecules such as proteins that are useful in the diagnosis and prognosis of cancer. As used herein, "cancer markers" include but are not limited to: PSA, human chorionic gonadotropin, alpha-fetoprotein, carcinoembryonic antigen, cancer antigen (CA) 125, CA 15-3, CD20, CDH13, CD31, CD34, CD105, CD146, D16S422HER-2, phospatidylinositol 3-kinase (PI 3-kinase), trypsin, trypsin-1 complexed with alpha(1)-antitrypsin, estrogen receptor, progesterone receptor, c-erbB-2, bcl-2, S-phase fraction (SPF), p185erbB-2, low-affinity insulin like growth factor-binding protein, urinary tissue factor, vascular endothelial growth factor, epidermal growth factor, epidermal growth factor receptor, apoptosis proteins (p53, Ki67), factor VIII, adhesion proteins (CD-44, sialyl-TN, blood group A, bacterial lacZ, human placental alkaline phosphatase (ALP), alpha-difluoromethylornithine (DFMO), thymidine phosphorylase (dTHdPase), thrombomodulin, laminin receptor, fibronectin, anticyclins, anticyclin A, B, or E, proliferation associated nuclear antigen, lectin UEA-1, and von Willebrand's factor.

The term "kallikrein" refers to a family of serine proteases found in tissues and body fluids of numerous animals including mammals and reptiles. The family of kallikreins includes enzymes such as hk1, a pancreatic renal kallikrein, human glandular kallikrein (hk2), and prostate-specific antigen (hk3). Plasma kallikrein usually circulates in the blood as pre-kininogen (HMWK). Following proteolysis, prekallikrein is activated to kallikrein which then cleaves HMWK to release bradykinin. The kallikreins, HMWK, and bradykinin represent some of the important proteins involved in the activation and inhibition of surface mediated pathways involved in blood clotting. As used herein, the term "kallikrein" refers to kallikrein analogs, homologs and active peptides thereof having the ability to regulate angiogenic activity.

The term "Protein-Specific Antigen" (PSA) refers generally to a protein that is approximately 26,000–32,000 Daltons in size as determined by ion-spray mass spectroscopy, more specifically to a protein that is 28,000–29,000 Daltons, and more preferably to a protein that is 28,430 Daltons. The amino acid sequence of a human PSA is provided in SEQ ID. NO: 1. The term PSA also includes precursor forms of the prepropeptide and propeptide as well as modified proteins and peptides that have a substantially similar amino acid sequence, and which are capable of inhibiting proliferation of endothelial cells. For example, silent substitutions of amino acids, wherein the replacement of an amino acid with a structurally or chemically similar amino acid does not significantly alter the structure, conformation or activity of the protein, are well known in the art. Such silent substitutions, additions and deletions, are intended to fall within the scope of the appended claims.

It will be appreciated that the term "PSA" includes shortened proteins or peptides wherein one or more amino acid is removed from either or both ends of PSA, or from an internal region of the protein, yet the resulting molecule retains angiogenic regulating activity. The term "PSA" also includes lengthened proteins or peptides wherein one or more amino acid is added to either or both ends of PSA, or to an internal location in the protein, yet the resulting molecule retains angiogenic regulating activity. Such molecules, for example with tyrosine added in the first position, are useful for labeling such as radioiodination with $^{125}$Iodine, for use in assays. Labeling with other radioisotopes may be useful in providing a molecular tool for isolating and identifying the target cell containing PSA receptors. Other labeling, with molecules such as ricin, may provide a mechanism for destroying cells with PSA receptors. The invention also contemplates that active peptides of PSA may be used alone or combined with other peptides and proteins to form chimeric proteins containing the active PSA peptide.

"Substantial sequence homology" means at least approximately 70% homology between amino acid residue sequence in the PSA analog homolog or derivative sequence and that of PSA, preferably at least approximately 80% homology, and more preferably at least approximately 90% homology.

PSA can be isolated from normal, hyperplastic, primary and metatstatic prostate tissue from a variety of species including humans. PSA can also be isolated from body fluids including, but not limited to, semen, serum, urine and ascites, or synthesized by chemical or biological methods (e.g. cell culture, recombinant gene expression, peptide synthesis and in vitro enzymatic catalysis of precursor molecules to yield active PSA). In addition, PSA may be produced from recombinant sources, from genetically altered cells implanted into animals, from tumors, and from cell cultures as well as other sources. Recombinant techniques include gene amplification from DNA sources using the polymerase chain reaction (PCR), and gene amplification from RNA sources using reverse transcriptase/PCR.

Though not wishing to be bound by the following theory, serine proteases and kallikreins such as PSA regulate angiogenic activity by specifically, and most likely reversibly, inhibiting endothelial cell proliferation. The inhibitor protein molecules of the present invention are useful as birth control drugs, and for treating angiogenesis-related diseases, particularly angiogenesis-dependent cancers and tumors. The protein molecules are also useful for curing angiogenesis-dependent cancers and tumors. The unexpected and surprising ability of these novel compounds to treat and cure angiogenesis-dependent cancers and tumors answers a long-felt, unfulfilled need in the medical arts, and provides an important benefit to mankind.

Important terms that are used herein are defined as follows. "Cancer" means angiogenesis-dependent cancers and tumors, i.e. tumors that require for their growth (expansion in volume and/or mass) an increase in the number and density of the blood vessels supplying them with blood. "Regression" refers to the reduction of tumor mass and size.

As used herein, the term "angiogenesis" and related terms such as "angiogenic" refer to activities associated with blood vessel growth and development, including, but not limited to, endothelial cell proliferation, endothelial cell migration and capillary tube formation.

As used herein, the term "antiangiogenic" refers to compositions and the like that are capable of inhibiting the formation of blood vessels, including but not limited to inhibiting endothelial cell proliferation, endothelial cell migration and capillary tube formation.

The process of angiogenesis is complex and involves a number of orchestrated steps that can be separately studied in vitro, such as FGF-2- and/or VEGF-stimulated endothelial cell proliferation and migration. For example, ANGIOSTATIN® protein and ENDOSTATIN® protein inhibit these processes (see U.S. Pat. Nos. 5,639,725 and 5,854,205, both of which are herein incorporated by reference). The inventors of the present invention have suprisingly discovered antiangiogenic properties of kallikreins, such as PSA, by demonstrating and systematically evaluating the effects of PSA on endothelial cell proliferation, migration, and invasion.

As explained in more detail in the Examples, the effects of PSA on angiogenic activity were first shown in Human Umbilical Vein Endothelial Cells (HUVEC). Purified human PSA demonstrated a potent and dose related inhibitory activity on FGF-2-stimulated proliferation of HUVEC cells, with an $IC_{50}$ (50% cell inhibition) of 4 $\mu M$ (see FIG. 4). To determine if PSA inhibited a variety of endothelial cells or simply displayed specificity for HUVECs, the ability of PSA to inhibit bovine adrenal cortex endothelial cell (BCE) and human microvascular dermal cell (HMVEC-d) proliferation was also evaluated. It was discovered that PSA potently inhibited FGF-2-stimulated endothelial cell proliferation, with an IC50 for BCE cells of 1.0 $\mu M$, and an $IC_{50}$ for HMVEC-d of 0.6 $\mu M$ (see FIGS. 5 and 6).

In order to demonstrate that PSA exerts antiangiogenic effects as opposed to general inhibition of cell proliferation, the inventors conducted experiments to evaluate direct stimulatory or inhibitory effect on the proliferation of cancer cells. As discussed in Example 6, the growth of murine melanoma cells (B16BL6) or human prostate cancer cells (PC3) was unaffected by the addition of purified human PSA (see FIGS. 7 and 8, respectively) thereby confirming PSA antiangiogenic activity.

The effects of PSA on endothelial cell migration were demonstrated by the inventors to further confirm the antiangiogenic effects of PSA. In order to evaluate the in vitro effects of PSA on endothelial cell migration in response to FGF-2 or VEGF, confluent monolayers of HUVEC were scraped to remove a section of monolayer and cultured with FGF-2 or VEGF in the presence or absence of purified human PSA (see Example 7). As shown in the figures, PSA exerted dose-response inhibitory effects on FGF-2 and VEGF-stimulated migration (see FIGS. 9 and 10 respectively).

The inventors further demonstrated antiangiogenic properties of PSA by evaluating its effects on endothelial cell invasion. As further discussed in the examples, the results of these experiments demonstrated that inhibition appeared to be dose dependent and not the result of toxicity since the endothelial cells appeared viable; and, although some elongation was noted, there were no junctions made by the endothelial cells. These findings demonstrate the inhibitory effects of PSA on endothelial cell invasion and further confirm PSA antiangiogenic activity.

Though not wishing to be bound by the following theory, it is believed that the antiangiogenic properties of PSA are related to its serine protease activity. As demonstrated by the inventors in Example 9, when the serine protease activity of PSA was blocked, the antiproliferative and antimigratory effects of PSA on endothelial cell were also inhibited.

As a result of their investigations, the inventors of the present invention have suprisingly demonstrated for the first time that PSA is an endothelial cell-specific inhibitor of angiogenesis that exhibits potent anti-proliferative and anti-migratory activity on a variety of cultured endothelial cells. Furthermore, PSA inhibits the endothelial-cell specific angiogenesis process of capillary tube formation in matrigel.

Based on the novel findings of the inventors, the present invention is directed to methods and compositions comprising the administration of serine proteases including kallikreins for the regulation of antiangiogenic processes. More particularly, the methods and compositions of the present invention comprise the administration of PSA for inhibiting angiogenesis and for reducing related cancer or tumor growth.

The antiangiogenic serine proteases of the present invention can be made by automated protein synthesis methodologies well-known to one skilled in the art. Alternatively, antiangiogenic serine proteases, or kallikreins, including PSA and peptide fragments thereof, may be isolated from larger known prepropeptides that share a common or similar amino acid sequence.

Proteins and peptides derived from these and other sources, including manual or automated protein synthesis, may be quickly and easily tested for antiangiogenic activity using a biological activity assay such as the human umbilical vein endothelial cell proliferation assay (HUVEC) and the bovine capillary endothelial cell proliferation assay (BCE). Such assays are described in U.S. Pat. No. 5,639,725 which is incorporated herein by reference. Other bioassays for inhibiting activity include the chick CAM assay, the mouse corneal assay, and the effect of administering isolated or synthesized proteins on implanted tumors. The chick CAM assay is described by O'Reilly, et al. in "Angiogenic Regulation of Metastatic Growth" *Cell*, vol. 79 (2), Oct. 21, 1994, pp. 315–328, which is hereby incorporated by reference in its entirety.

Applicants' invention also encompasses nucleic acid sequences that correspond to, and code for the antiangiogenic serine proteases of the invention, and to monoclonal and polyclonal antibodies that bind specifically to such protein molecules. The biologically active protein molecules, nucleic acid sequences corresponding to the proteins, and antibodies that bind specifically to the proteins of the present invention are useful for modulating angiogenic processes in vivo, and for diagnosing and treating endothelial cell-related diseases, for example by gene therapy.

Nucleic acid sequences that correspond to, and code for, serine proteases and kallikreins such as PSA and PSA analogs, can be prepared based upon the knowledge of the amino acid sequence, and the art recognized correspondence between codons (sequences of three nucleic acid bases), and amino acids. Because of the degeneracy of the genetic code, wherein the third base in a codon may vary yet still code for the same amino acid, many different possible coding nucleic acid sequences are derivable for any particular protein or peptide fragment.

Nucleic acid sequences are synthesized using automated systems well known in the art. Either the entire sequence may be synthesized or a series of smaller oligonucleotides are made and subsequently ligated together to yield the full length sequence. Alternatively, the nucleic acid sequence may be derived from a gene bank using oligonucleotides probes designed based on the N-terminal amino acid sequence and well known techniques for cloning genetic material.

The present invention also encompasses gene therapy whereby a gene encoding serine proteases including kallikreins such as the gene encoding PSA, is regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335–356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a gene such as that for PSA may be placed in a patient and thus prevent occurrence of angiogenesis; or a gene that makes tumor cells more susceptible to radiation could be inserted and then radiation of the tumor would cause increased killing of the tumor cells.

Many protocols for transfer of serine protease or kallikrein DNA, or kallikrein regulatory sequences are envisioned in this invention. Transfection of promoter sequences, other than one normally found specifically associated with kallikrein, or other sequences which would increase production of kallikreins are also envisioned as methods of gene therapy. An example of this technology is found in Transkaryotic Therapies, Inc., of Cambridge, Mass., using homologous recombination to insert a "genetic switch" that turns on an erythropoietin gene in cells. See Genetic Engineering News, Apr. 15, 1994. Such "genetic switches" could be used to activate kallikreins (or kallikreins receptors) in cells not normally expressing kallikrein (or the kallikrein receptor).

Gene transfer methods for gene therapy fall into three broad categories: physical (e.g., electroporation, direct gene transfer and particle bombardment), chemical (lipid-based carriers, or other non-viral vectors) and biological (virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of kallikrein DNA or kallikrein regulatory sequences.

Chemical methods of gene therapy may involve a lipid based compound, not necessarily a liposome, to ferry the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Gene regulation of serine proteases such as kallikreins may be accomplished by administering compounds that bind to kallikrein genes, or control regions associated with the kallikrein genes, or corresponding RNA transcript to modify the rate of transcription or translation. Additionally, cells transfected with a DNA sequence encoding kallikreins may be administered to a patient to provide an in vivo source of kallikrein. For example, cells may be transfected with a vector containing a nucleic acid sequence encoding kallikreins. The term "vector" as used herein means a carrier that can contain or associate with specific nucleic acid sequences, which functions to transport the specific nucleic acid sequences into a cell. Examples of vectors include plasmids and infective microorganisms such as viruses, or non-viral vectors such as ligand-DNA conjugates, liposomes, lipid-DNA complexes. It may be desirable that a recombinant DNA molecule comprising a kallikrein DNA sequence is operatively linked to an expression control sequence to form an expression vector capable of expressing a kallikrein. The transfected cells may be cells derived from the patient's normal tissue, the patient's diseased tissue, or may be non-patient cells.

For example, tumor cells removed from a patient can be transfected with a vector capable of expressing a kallikrein protein of the present invention, and re-introduced into the patient. The transfected tumor cells produce kallikrein levels in the patient that inhibit the growth of the tumor. Patients may be human or non-human animals. Cells may also be transfected by non-vector, or physical or chemical methods known in the art such as electroporation, incorporation, or via a "gene gun." Additionally, kallikrein DNA may be directly injected, without the aid of a carrier, into a patient. In particular, kallikrein DNA may be injected into skin, muscle or blood.

The gene therapy protocol for transfecting kallikrein into a patient may either be through integration of kallikrein DNA into the genome of the cells, into minichromosomes or as a separate replicating or non-replicating DNA construct in the cytoplasm or nucleoplasm of the cell. Kallikrein expression may continue for a long-period of time or may be reinjected periodically to maintain a desired level of kallikrein protein in the cell, the tissue or organ or a determined blood level.

The present invention includes methods of treating or preventing angiogenic diseases and processes including, but not limited to, arthritis and tumors by stimulating the production of serine proteases including kallikreins such as PSA, and/or by administering substantially purified kallikreins, or kallikrein agonists or antagonists, and/or kallikrein antisera to a patient. Additional treatment methods include administration of kallikreins, kallikrein fragments, kallikrein antisera, or kallikrein receptor agonists and antagonists linked to cytotoxic agents. It is to be understood that kallikreins can be animal or human in origin. Kallikreins can also be produced synthetically by chemical reaction or by recombinant techniques in conjunction with expression systems. Kallikreins can also be produced by enzymatically cleaving different molecules, including kallikrein precursors, containing sequence homology or identity with segments of kallikreins to generate peptides having anti-angiogenesis activity.

Antibodies that specifically bind kallikreins can be employed to modulate endothelial-dependent processes such as reproduction, development, and wound healing and tissue repair. In addition, antisera directed to the Fab regions of kallikrein antibodies can be administered to block the ability of endogenous kallikrein antisera to bind kallikreins.

Antibodies specific for serine proteases, kallikreins and/or PSA, and kallikrein and PSA analogs, are made according to techniques and protocols well known in the art. The antibodies may be either polyclonal or monoclonal. The antibodies are utilized in well know immunoassay formats, such as competitive and non-competitive immunoassays, including ELISA, sandwich immunoassays and radioimmunoassays (RIAs), to determine the presence or absence of the endothelial proliferation inhibitors of the present invention in body fluids. Examples of body fluids include but are not limited to semen, blood, serum, peritoneal fluid, pleural fluid, cerebrospinal fluid, uterine fluid, saliva, and mucus.

The proteins, nucleic acid sequences and antibodies of the present invention are useful for diagnosing and treating endothelial cell-related diseases and disorders. A particularly important endothelial cell process is angiogenesis, the formation of blood vessels. Angiogenesis-related diseases may be diagnosed and treated using the endothelial cell proliferation inhibiting proteins of the present invention. Angiogenesis-related diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis blindness; plaque neovascularization; telangiectasia; hemophiliac joints; angiofibroma; and wound granulation. The endothelial cell proliferation inhibiting proteins of the present invention are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (*Rochele minalia quintosa*) and ulcers (*Helicobacter pylorii*).

The angiogenic regulating proteins of the present invention can be used as a birth control agent by reducing or preventing uterine vascularization required for embryo implantation. Thus, the present invention provides an effective birth control method when an amount of the inhibitory kallikrein protein sufficient to prevent embryo implantation is administered to a female. In one aspect of the birth control method, an amount of the inhibiting protein sufficient to block embryo implantation is administered before or after intercourse and fertilization have occurred, thus providing an effective method of birth control, possibly a "morning after" method. While not wanting to be bound by this statement, it is believed that inhibition of vascularization of the uterine endometrium interferes with implantation of the blastocyst. Similar inhibition of vascularization of the mucosa of the uterine tube interferes with implantation of the blastocyst, preventing occurrence of a tubal pregnancy. Administration methods may include, but are not limited to, pills, injections (intravenous, subcutaneous, intramuscular), suppositories, vaginal sponges, vaginal tampons, and intrauterine devices. It is also believed that kallikrein administration will interfere with normal enhanced vascularization of the placenta, and also with the development of vessels within a successfully implanted blastocyst and developing embryo and fetus.

Conversely, blockade of serine protease or kallikrein receptors, such as PSA receptors with PSA analogs which act as receptor antagonists, may promote angiogenic activity such as endothelialization and vascularization. Such effects may be desirable in situations of inadequate vascularization of the uterine endometrium and associated infertilty, wound repair, healing of cuts and incisions, treatment of vascular problems in diabetics, especially retinal and peripheral vessels, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

The present invention also relates to methods of using kallikreins and angiogenic peptide fragments of kallikreins, nucleic acid sequences corresponding to kallikreins and active peptide fragments thereof, and antibodies that bind specifically to PSA and related peptides, to diagnose endothelial cell-related diseases and disorders.

The invention further encompasses a method for identifying kallikrein-specific receptors, and the receptor molecules identified and isolated thereby. The present invention also provides a method for quantitation of kallikrein receptors.

A particularly important aspect of the present invention is administration of kallikreins such as PSA either alone or in combination with one or more anti-angiogenic agents, such as ENDOSTATIN® protein, ANGIOSTATIN® protein, or METASTATIN™ protein (Entremed, Inc., Rockville, Md.), in an amount sufficient to inhibit tumor growth and cause sustainable regression of tumor mass to microscopic size. Accordingly, the present invention also includes formulations effective for treating or curing angiogenesis-dependent cancers and tumors.

More particularly, recombinant PSA, from insect cells or E. coli, for example, can potently inhibit angiogenesis and the growth of metastases. It is contemplated as part of the present invention that PSA can be isolated from a body fluid such as semen, blood or urine of patients, or that PSA can be produced by recombinant DNA methods or synthetic peptide chemical methods that are well known to those of ordinary skill in the art. Protein purification methods are well known in the art and an assay for inhibitory activity is provided in the examples below.

One example of a method of producing serine proteases or kallikreins such as PSA using recombinant DNA techniques entails the steps of (1) identifying and purifying PSA as discussed above, and as more fully described below, (2) determining the N-terminal amino acid sequence of the purified inhibitor, (3) synthetically generating a DNA oligonucleotide probe that corresponds to the N-terminal amino acid sequence, (4) generating a DNA gene bank from human or other mammalian DNA, (5) probing the gene bank with the DNA oligonucleotide probe, (6) selecting clones that hybridize to the oligonucleotide, (7) isolating the inhibitor gene from the clone, (8) inserting the gene into an appropriate vector such as an expression vector, (9) inserting the gene-containing vector into a microorganism or other expression system capable of expressing the inhibitor gene, and (10) isolating the recombinantly produced inhibitor. The above techniques are more fully described in laboratory manuals such as "Molecular Cloning: A Laboratory Manual" Latest Edition by Sambrook et al., Cold Spring Harbor Press, 1989.

Yet another method of producing kallikreins, PSA, or biologically active fragments thereof, is by peptide synthesis. For example, once a biologically active fragment of PSA is found, it can be sequenced, for example by automated peptide sequencing methods. Alternatively, once the gene or DNA sequence which codes for PSA is isolated, for example by the methods described above, the DNA sequence can be determined, which in turn provides information regarding the amino acid sequence. Thus, if the biologically active fragment is generated by specific methods, such as tryptic digests, or if the fragment is N-terminal sequenced, the remaining amino acid sequence can be determined from the corresponding DNA sequence.

Once the amino acid sequence of the peptide is known, for example the N-terminal 20 amino acids, the fragment can be synthesized by techniques well known in the art, as exemplified by "Solid Phase Peptide Synthesis: A Practical Approach" E. Atherton and R. C. Sheppard, IRL Press, Oxford England. Similarly, multiple fragments can be synthesized which are subsequently linked together to form larger fragments. These synthetic peptide fragments can also be made with amino acid substitutions at specific locations in order to test for agonistic and antagonistic activity in vitro and in vivo.

The synthetic peptide fragments of kallikreins such as PSA have a variety of uses. The peptide that binds to the PSA receptor with high specificity and avidity is radiolabeled and employed for visualization and quantitation of binding sites using autoradiographic and membrane binding techniques. Knowledge of the binding properties of the PSA receptor facilitates investigation of the transduction mechanisms linked to the receptor.

Different peptide fragments of the intact PSA molecule can be synthesized for use in several applications including, but not limited to the following; as antigens for the development of specific antisera, as agonists and antagonists active at PSA binding sites, as peptides to be linked to cytotoxic agents for targeted killing of cells that bind PSA. The amino acid sequences that comprise these peptides are selected on the basis of their position on the exterior regions of the molecule and are accessible for binding to antisera. Peptides can be synthesized in a standard microchemical facility and purity checked with HPLC and mass spectrophotometry. Methods of peptide synthesis, HPLC purification and mass spectrophotometry are commonly known to those skilled in these arts.

PSA and PSA peptides can also be produced in recombinant E. coli, or in insect or yeast expression systems, and purified with column chromatography.

PSA peptides can be chemically coupled to isotopes, enzymes, carrier proteins, cytotoxic agents, fluorescent molecules and other compounds for a variety of applications. The efficiency of the coupling reaction is determined using different techniques appropriate for the specific reaction.

Systematic substitution of amino acids within the synthesized peptides yields high affinity peptide agonists and antagonists to kallikrein receptors that enhance or diminish kallikrein binding to its receptor. Such agonists are used to suppress the growth of primary and metastatic tumors, thereby limiting the spread of cancer. Antagonists to kallikrein are applied in situations of inadequate vascularization, to block the inhibitory effects of kallikrein and possibly promote angiogenesis. This treatment may have therapeutic effects to promote wound healing in diabetics.

PSA peptides are employed to develop affinity columns for isolation of the PSA receptor from cultured cells. Isolation and purification of the PSA receptor is followed by amino acid sequencing. Next, nucleotide probes are developed for insertion into vectors for expression of the receptor. These techniques are well known to those skilled in the art. These techniques can be helpful in defining minimal structures of PSA for receptor engagement.

Cytotoxic agents, such as ricin, are linked to PSA, and high affinity PSA peptide fragments, thereby providing a tool for destruction of cells that bind PSA. These cells may be found in many locations, including but not limited to, metastases and primary tumors. Peptides linked to cytotoxic agents are infused in a manner designed to maximize delivery to the desired location. For example, ricin-linked high affinity PSA fragments are delivered through a cannula into vessels supplying the target site or directly into the target. Such agents are also delivered in a controlled manner through osmotic pumps coupled to infusion cannulae. A combination of PSA antagonists may be co-applied with stimulators of angiogenesis to increase vascularization of tissue.

Antiserum against kallikrein can be generated. After peptide synthesis and purification, both monoclonal and polyclonal antisera are raised using established techniques known to those skilled in the art. For example, polyclonal antisera may be raised in rabbits, sheep, goats or other animals. Kallikrein peptides conjugated to a carrier molecule such as bovine serum albumin, are combined with an adjuvant mixture, emulsified and injected subcutaneously at multiple sites on the back, neck, flanks, and sometimes in the footpads. Booster injections are made at regular intervals, such as every 2 to 4 weeks. Blood samples are obtained by venipuncture, for example using the marginal ear veins after dilation, approximately 7 to 10 days after each injection. The blood samples are allowed to clot overnight at 4° C. and are centrifuged at approximately 2400×g at 4° C. for about 30 minutes.

All serum samples from generation of polyclonal antisera or media samples from production of monoclonal antisera are analyzed for determination of titer. Titer is established through several means, for example, using dot blots and density analysis, and also with precipitation of radiolabeled peptide-antibody complexes using protein A, secondary antisera, cold ethanol or charcoal-dextran followed by activity measurement with a gamma counter. The highest titer antisera are also purified on affinity columns which are commercially available. PSA peptides are coupled to the gel in the affinity column. Antiserum samples are passed through the column and anti- PSA antibodies remain bound to the column. These antibodies are subsequently eluted, collected and evaluated for determination of titer and specificity.

The highest titer PSA antisera is tested to establish the following; a) optimal antiserum dilution for highest specific binding of the antigen and lowest non-specific binding, b) the ability to bind increasing amounts of PSA peptide in a standard displacement curve, c) potential cross-reactivity with related peptides and proteins, including PSA related species, d) ability to detect PSA peptides in extracts of, semen, plasma, urine, tissues, and in cell culture media.

According to the present invention, kallikreins such as PSA may be used in combination with other compositions and procedures for the treatment of diseases. For example, a tumor may be treated conventionally with surgery, radiation or chemotherapy combined with or without PSA and then PSA may be subsequently administered to the patient to extend the dormancy of micrometastases and to stabilize any residual primary tumor.

It is to be understood that the present invention is contemplated to include any derivatives of serine proteases and kallikreins that have angiogenic activity. The present invention includes the entire PSA protein, derivatives of the PSA protein and biologically-active fragments of the PSA protein. These include proteins with PSA activity that have amino acid substitutions or have sugars or other molecules attached to amino acid functional groups. The present invention also includes genes that code for kallikreins and kallikrein receptors, and to proteins that are expressed by those genes.

The serine protease proteins and protein fragments having antiangiogenic activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the proteins may be incorporated into biodegradable polymers allowing for sustained release of the compound, the polymers being implanted in the vicinity of where drug delivery is desired, for example, at the site of a tumor or implanted so that the kallikrein is slowly released systemically. Osmotic minipumps may also be used to provide controlled delivery of high concentrations of kallikreins through cannulae to the site of interest, such as directly into a metastatic growth or into the vascular supply to that tumor. The biodegradable polymers and their use are described, for example, in detail in Brem et al., *J. Neurosurg.* 74:441–446 (1991), which is hereby incorporated by reference in its entirety.

The serine protease formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. Kallikrein formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

The dosage of the serine protease composition of the present invention will depend on the disease state or condition being treated and other clinical factors such as weight and condition of the human or animal and the route of administration of the compound. For treating humans or animals, between approximately 0.5 to 500 mg/kilogram is typical broad range for administering a serine protease or kallikrein protein such as PSA. Depending upon the half-life of the protein in the particular animal or human, the protein can be administered between several times per day to once a week. It is to be understood that the present invention has application for both human and veterinary use. The methods of the present invention contemplate single as well as multiple administrations, given either simultaneously or over an extended period of time.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Effect of PSA on bFGF-induced Proliferation of HUVE Cells

Proliferation assays familiar to those skilled in the art using human umbilical vein endothelial (HUVE) cells were used to determine the effect of PSA on bFGF-induced proliferation of human umbilical vein endothelial cells.

The materials for this experiment included HUVE cells and media for their proliferation, Endothelial Cell Basal Medium (EBM) and Endothelial Cell Growth Medium (EGM), (Clonetics, San Diego, Calif.). Also used was Human Prostate-Specific Antigen, (Vitro Diagnostics, Inc. Littleton, Colo. catalog number 4-70-455).

The proliferation assay involved the routine culturing HUVE cells to confluency in EGM media. The cells were trypsinized and plated in a 96-well plate at 5000 cells per well per 100 mL EBM media. The cells were plated in EBM for 24 hours. Next bFGF at 5 ng/ml and PSA at various concentrations were added to the wells (1–100 µg/ml). The cells were cultured for 72 hours after which cell proliferation was determined using a standard bromo-uridine incorporation method.

Results

PSA inhibited bFGF-induced proliferation of HUVE cells in a dose dependent manner in two different experiments. The relative inhibitory effects of the various concentrations of PSA are shown graphically in FIGS. 1, 2 and 4 respectively.

Example 2

Effect of PSA on bFGF-induced Proliferation of BCE Cells

Proliferation assays familiar to those skilled in the art using bovine capillary endothelial cells (BCE) were used to determine the effect of PSA on bFGF-induced proliferation of BCE Cells.

Materials and Methods

The materials for this experiment included BCE cells and media for their proliferation, Endothelial Cell Basal Medium (EBM) and Endothelial Cell Growth Medium (EGM), (Clonetics, San Diego, Calif.). Also used was Human Prostate-Specific Antigen, (Vitro Diagnostics, Inc. Littleton, Colo. catalog number 4-70-455).

The cells were cultured for 72 hours after stimulation with bFGF in the presence or absence of PSA at various concentrations as indicated on FIG. 3.

Results

PSA inhibited bFGF-induced proliferation of BCE cells in a dose dependent manner. The relative inhibitory effects of the various concentrations of PSA are shown graphically in FIGS. 3 and 5.

Example 3

In Vivo Effect of PSA on Tumor Growth

PSA (Vitro Diagnostics, Inc. Littleton, Colo. catalog number. 4-70-455) was used to treat mice that had been inoculated with B16BL6Melanoma. The mice were inoculated with $5 \times 10^4$ tumor cells intraveneously on day 0. On day 3 and for the next consecutive 11 days, the animals were treated with PBS or 30 µg of a) PSA; 9 µM, or b) a control protein; 15 µM, or c) ENDOSTATIN® as a positive control; 15 µM. The mice were sacrificed at day 14 and the lung metastases were counted. The mean number of lung metastases for each of the treated groups was compared with the PBS control to give a T/C (treated/control) ratio.

Results

As summarized below, mice receiving a PSA treatment had a significantly lower occurrence of lung metastases as compared to control mice. PSA demonstrated modest growth inhibitory effects on tumor lesions in mouse lungs (20 and 40% inhibition).

Effect of PSA on Metastatic (B16B16) Disease in Mice

| Treatment | Dose: | Mean Lung Metastases ±1S.D. of the Mean: | T/C: | p value: |
|---|---|---|---|---|
| PBS | 0.1 ml | 115 ± 16 | 1.0 | — |
| PSA | 9 µM | 70 ± 8 | 0.61 | 0.003 |
| Negative Control | 15 µM | 88 ± 10 | 0.77 | 0.044 |
| ENDOSTATINO Protein | 15 µM | 16 ± 8 | 0.14 | 0.0002 |

Example 4

Antiproliferative Effects of PSA

The antiproliferative effects of PSA were demonstrated in Human Umbilical Vein Endothelial Cells (HUVEC).

Human umbilical vein endothelial cells (HUVEC): Single donor HUVEC were obtained frozen at passage 1 from Clonetics (San Diego, Calif.). The cells were maintained in endothelial cell growth medium (EGM, Clonetics) supplemented with bovine brain extract (Clonetics). Cells were cultured on 75 cm² vented tissue culture flasks (Costar Corning, NY) at 37° C., in moist air containing 5% $CO_2$. HUVEC were used at passages 2–5 in all following examples. For proliferation assays HUVEC were obtained from trypsin/versene (Biowhittaker, Walkersville, Md.) digested monolayers. Cells were resuspended in endothelial cell basal medium-2 (EBM-2, Clonetics) supplemented with 2% heat inactivated FBS (Hyclone, Logan, Utah.) and 2 mM L-glutamine (Biowhittaker). Two hundred µL of HUVEC at 2.5×104/mL were plated into 96 well flat bottom plates (Costar) and incubated overnight at 37° C. in 5% $CO_2$. These cultures were then washed and exposed to various concentrations of purified human PSA (Vitro Diagnostics, Littleton, Colo.) or to media alone in a total volume of 100 µL and incubated for 30 minutes at 37° C. in 5% $CO_2$. After 30 minutes of incubation, an additional 100 µL of assay media containing 10 ng/mL of FGF-2 (R&D Systems, Minneapolis, Minn.) was added to all cultures except for the control which contained media alone. All cultures were incubated for an additional 48 h at 37° C. in 5% $CO_2$. Cell proliferation was assessed with a colorimetric ELISA kit (Boehringer Mannheim, Indianapolis, Ind.) that measured the amount of BrdU incorporated during DNA Synthesis. Results are expressed as the mean absorbance of triplicate cultures measured at 370 nm (reference wavelength 492 nm).

As shown in FIG. 4, purified human PSA demonstrated a potent and dose related inhibitory activity on FGF-2- stimulated proliferation of HUVEC cells, with an $IC_{50}$ (50% cell inhibition) of 4 $\mu$M.

Example 5

Antiproliferative Effects of PSA on Cells Other Than HUVECs

Figure 5:
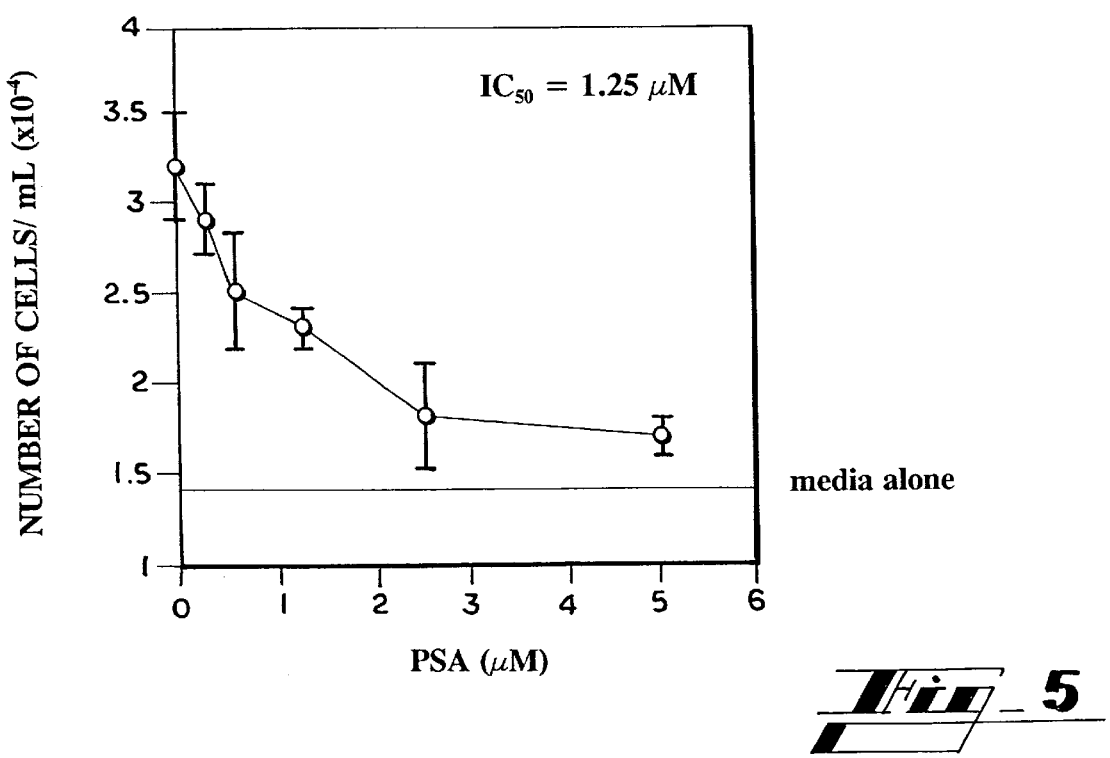
FIG. 5 is a graph showing the effects of PSA on proliferation of bovine capillary endothelial cells (BCE) in vitro.

To determine if PSA inhibited a variety of endothelial cells or simply displayed specificity for HUVECs, the ability of PSA to inhibit bovine adrenal cortex endothelial cell (BCE) and human microvascular dermal cell (HMVEC-d) proliferation was also evaluated (see FIGS. 5 and 6).

BCE were obtained at passage 9 as a generous gift from Dr. J. Folkman, (Children's Hospital, Harvard Medical School, Boston, Mass.). The cells were cultured and maintained as described by O'Reilly Cell 79:315 (1994). For evaluation of PSA ability to inhibit BCE proliferation, assays were performed also as described O'Reilly and cells were exposed to various concentrations of purified PSA or media alone for 30 minutes at 37° C. in 10% $CO_2$ prior to stimulation with FGF-2. Cell proliferation was assessed by counting the number of cells with a Coulter Z1 particle counter (Coulter Corp., Hialeah, Fla.). Results are expressed as the mean number of cells counted in triplicate culture wells.

Single donor adult HMVEC-d were obtained frozen at passage 4 from Clonetics. The cells were maintained in microvascular endothelial cell growth medium-2 (EGM-2-MV, Clonetics). Cells were cultured on 75 $cm^2$ vented tissue culture flasks at 37° C., in moist air containing 5% $CO_2$. HMVEC-d were used at passages 5–8 in all experiments. For proliferation assays HMVEC-d were obtained from trypsin/versene (Biowhittaker) digested monolayers. HMVEC-d were resuspended in endothelial cell basal medium-2 (EBM-2, Clonetics) supplemented with 2% heat inactivated FBS (Hyclone) and 2 mM L-glutamine. Cells at 1.6×104/ml were plated into 1.5% gelatin coated 24 well flat bottom plates (Costar) and incubated overnight at 37° C. in 5% $CO_2$. These cultures were then washed and exposed to various concentrations of purified PSA or to media alone and incubated for 30 minutes at 37° C. in 5% $CO_2$. After 30 minutes FGF-2 at 10 ng/mL was added to all cultures except for the control which contained media alone. All cultures were incubated for an additional 48 h at 37° C. in 5% $CO_2$. Cell proliferation was assessed by counting the number of cells/well with a Coulter Z1 particle counter (Coulter Corp). Results are expressed as the mean number of cells counted in triplicate culture wells.

As shown in FIGS. 5 and 6. PSA potently inhibited FGF-2-stimulated endothelial cell proliferation, with an $IC_{50}$ for BCE cells of 1.0 $\mu$M, and an $IC_{50}$ for HMVEC-d of 0.6 $\mu$M. Accordingly, inventors effectively demonstrated that the antiproliferative effects of PSA were not limited to, or specific for, HUVECs.

Example 6

Specificity of Anti-Proliferative Effects of PSA

In order to demonstrate that the antiproliferative effects of PSA are specific for endothelial cells, the inventors conducted experiments to evaluate direct stimulatory or inhibitory effect on the proliferation of cancer cells.

B16BL6, a murine melanoma, obtained from the NCI-FCRC cell repository were maintained in DMEM (Biowhittaker), supplemented with 5% heat inactivated fetal bovine serum FBS (Hyclone) and 2 mM L-glutamine. Tumor cells were cultured on 75 cm2 vented tissue culture flasks at 37° C., 5% $CO_2$ in moist air. For proliferation assays B16BL6 were obtained from trypsin/versene (Biowhittaker) digested monolayers. B16BL6 at 1.25×104/ml were plated into 96 well flat bottom plates (Costar) and incubated overnight at 37° C. in 5% CO. These cultures were then washed and exposed to various concentrations of purified PSA or media alone and incubated for an additional 48 h at 37° C. in 5% $CO_2$. Tumor lines showed FGF-2 independent growth in vitro. Cell proliferation was assessed with a colorimetric ELISA kit (Boehringer Mannheim) for BrdU incorporation. Results are expressed as the mean absorbance of triplicate cultures measured at 370 nm (reference wavelength 492 nm).

Human prostate cancer cell line, PC3, also a kind gift from Dr. Folkman. PC3 were used to determine PSA inhibitory effects on FGF-2 independent cell growth. PC3 were obtained by gentle removal of cells from the tissue culture flask with a cell scraper (Costar). Cells were resuspended in DMEM supplemented with 10% heat inactivated FBS and 2mM L-glutamine, plated into 24 well flat bottom plates at 6×104/mL (Costar) and incubated overnight at 37° C. in 5% $CO_2$. These cultures were then washed and exposed to various concentrations of purified PSA or to media alone (no FGF-2 added to the cultures) and incubated for 30 minutes at 37° C. in 5% $CO_2$. After 30 minutes of incubation, additional assay media was added to all wells. All cultures were incubated for an additional 48 hours at 37° C. in 5% $CO_2$. Cell proliferation was assessed by counting the number of cells with a Coulter Z1 particle counter. Results are expressed as the mean number of cells in triplicate cultures.

As shown in the figures, the growth of murine melanoma cells (B16BL6) or human prostate cancer cells (PC3) was unaffected by the addition of purified human PSA (see FIGS. 7 and 8, respectively).

Example 7

Anti-Migratory Effects of PSA on Endothelial Cells

In order to evaluate the in vitro effects of PSA on endothelial cell migration in response to FGF-2 or VEGF, confluent monolayers of HUVEC were scraped to remove a section of monolayer and cultured for 24 hr with FGF-2 or VEGF in the presence or absence of purified human PSA.

A wound migration assay was performed as described by Kubota et al. J. Cell Biol. 107:1589 (1988) to determine the ability of PSA to block HUVEC migration induced by recombinant FGF-2 or recombinant VEGF 165 (R&D Systems). Briefly, 5×105 HUVEC in EGM were plated onto 1.5% gelatin coated 60 mm tissue culture dishes (Corning) and incubated for 72 h at 37° C. in 5% $CO_2$ in moist air. After incubation, confluent monolayers were wounded with a sterile single edged No. 9 razor blade (VWR Scientific, Media, Pa.) which resulted in a straight edge that separates the confluent area from the denuded area. Immediately after monolayers were wounded, the cells were washed with PBS (Biowhittaker) to remove cellular debris, and further incubated in EBM supplemented with 1% heat inactivated FBS, 2 mM L-glutamine, 100 $\mu$/ml penicillin, 100 $\mu$g/ml streptomycin and 0.25 $\mu$g/ml fungizone. The monolayers were exposed to 2 ng/mL of FGF-2 or to 10 ng/mL VEGF in the presence or absence of different concentrations of PSA (Vitro Diagnostics), or to media alone for 16–20 h in 5% $CO_2$ in moist air. The monolayers were fixed with absolute methanol and stained with Hematoxylin Solution, Gill No.3 (Sigma Diagnostics, St. Louis, Mo.). Migration was quantified by counting the number of cells that Migrated from the wound edge into the denuded area. Cells were counted at 200x magnification using an inverted light microscope with an ocular micrometer along a 1 cm distance. The values represent the mean number of cells in duplicate cultures.

Figure 10:
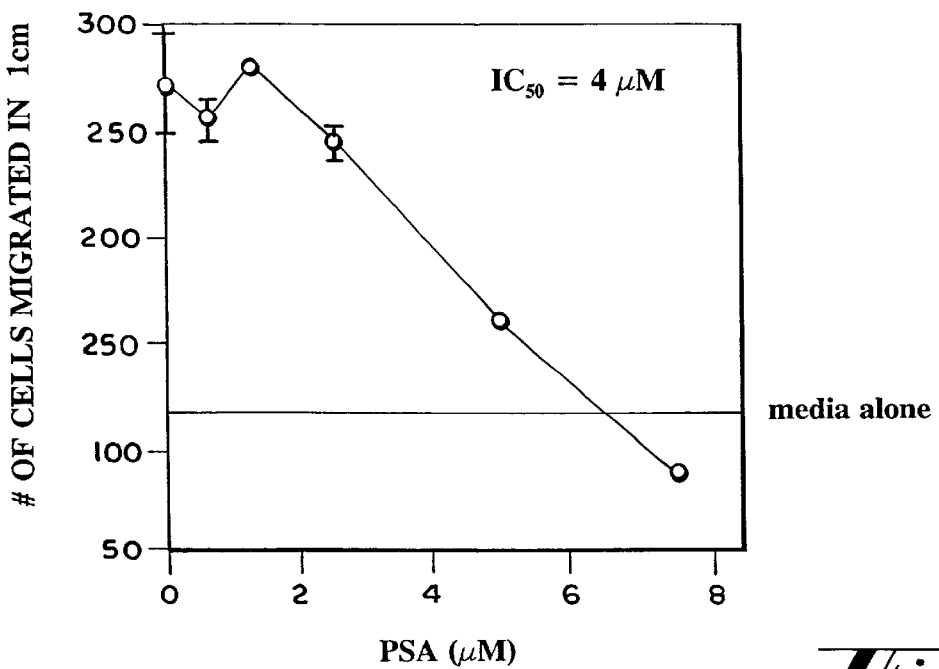
FIG. 10 is a graph showing the effects of PSA on migration of VEGF-stimulated HUVECs.

As shown in figures, PSA exerted dose-response inhibitory effects on FGF-2 and VEGF-stimulated migration, respectively, with an $IC_{50}$ for PSA versus FGF-2 of 1.2 $\mu$M, and versus VEGF of 4 $\mu$M (see FIGS. 9 and 10).

Example 8

Effect of PSA on Invasion by Endothelial Cells

Assays to measure migration of endothelial cells were coupled with another parameter of angiogenesis, invasion, by performing the assay in a two-chamber environment where the chambers are separated with a membrane filter coated with matrigel. In this assay, PSA, at 5 $\mu$M, inhibited FGF-2-stimulated HUVEC invasion through matrigel by 77%. In addition, at concentrations ranging from 0.3 $\mu$M to 3 $\mu$M purified human PSA inhibited tube formation of HUVEC in matrigel by approximately 50% (26, not shown).

Biocoat matrigel 8 $\mu$m invasion chambers (Collaborative Biomedical Products, Bedford, Mass.) were precoated with 38 $\mu$g of matrigel (Collaborative Biomedical Products). Chambers were rehydrated with warm (37° C.) EBM supplemented with 1% heat inactivated FBS and 2 mM L-glutamine for 2 h at room temperature. After rehydration, the media was gently removed and replaced immediately with 5×104 HUVEC pretreated with PSA (5 $\mu$M) or with media alone for 30 minutes at 37° C. in 5% $CO_2$. The lower chambers were filled with assay media supplemented with 5 ng/mL of FGF-2 or assay media alone. These chambers were then incubated for 24 h at 37° C. in 5% $CO_2$. After incubation, the non-invading cells were removed by scrubbing the inserts with a cotton swab. The cells on the lower surface of the membrane were stained with Diff-Quik (Dade Diagnostics, Aquado, PR). The membrane was removed and mounted on a microscope slide. The number of cells invaded was determined by counting the cells in the central field of the membrane of triplicate cultures within a 24×36 mm ocular grid at 150x magnification.

Matrigel obtained from Collaborative Biomedical Products (Bedford, Mass.) exists as a liquid below 4° C. and forms a gel at temperatures above 4° C. For induction of endothelial tube formation the following procedure was adapted from the protocol of Kubota et al. Briefly, matrigel is aliquoted into a 96 well tissue culture plate (Costar) in a volume of 65 $\mu$L. The plate is incubated for 30 min at 37° C. to allow the matrigel to gel. Following incubation, various doses of PSA (Vitro Diagnostics) were added to the matrigel in a volume of 100 $\mu$L. Included as a positive control was 2-methoxyestradiol (Fotsis Nature and media alone served as negative control. The HUVECs were harvested and adjusted to 1×10$^5$ cells/ml in EGM supplemented with 5% heat inactivated FBS. HUVEC at passages >p6 were not able to form tubes. One hundred $\mu$L cell suspension was added to the wells and incubated at 37° C., 5% $CO_2$ in moist air. After 4 hours of incubation, endothelial cells elongate and tube structures begin to form by 16 hrs endothelial cells are microscopically evaluated for tube formation.

The results of this experiment demonstrated that inhibition appeared to be dose dependent and not the result of toxicity; endothelial cells appeared viable (although no viability count was performed), and some elongation was noted but, there were no junctions made by the endothelial cells.

Example 9

Effect of PSA Serine Protease Activity on Angiogenesis

PSA has serine protease activity, and in serum, PSA is predominantly bound to the protease inhibitor, alpha-1 antichymotrypsin (ACT) (Lilia et al. Clin. Chem. 37:9 (1991)). The ability of ACT to inhibit both serine protease activity of purified PSA as well as the antimigratory effects of PSA on FGF-2-stimulated HUVEC was tested as described below.

The ability of $\alpha_1$-antichymotrypsin to inhibit the proteolytic activity of PSA was measured using the synthetic substrate S-2586 (MeO-Suc-Arg-Pro-Tyr-NH-Np). The rate of hydrolysis of S-2586 (1.3 mM) by PSA 6 $\mu$g (0.89 $\mu$M) with and without pretreatment for 4 hours at 37° C. with an equimolar concentration of ACT (Sigma Chemical Co., St. Louis, Mo.) was monitored at 405 nm in 50 mM Tris/HCl, pH 7.8 containing 0.1 M NaCl. Stable complexes of PSA and ACT formed after 4 hours of incubation and were confirmed by SDS-PAGE. The results were plotted as an increase in absorbance vs time in minutes. The ability of ACT (Sigma) to inhibit the anti-migratory activity of PSA was measured by preincubating PSA (5 $\mu$M) with an equimolar concentration of ACT for 4 h at 37° C. prior to addition to the HUVEC migration assay.

Figure 11:
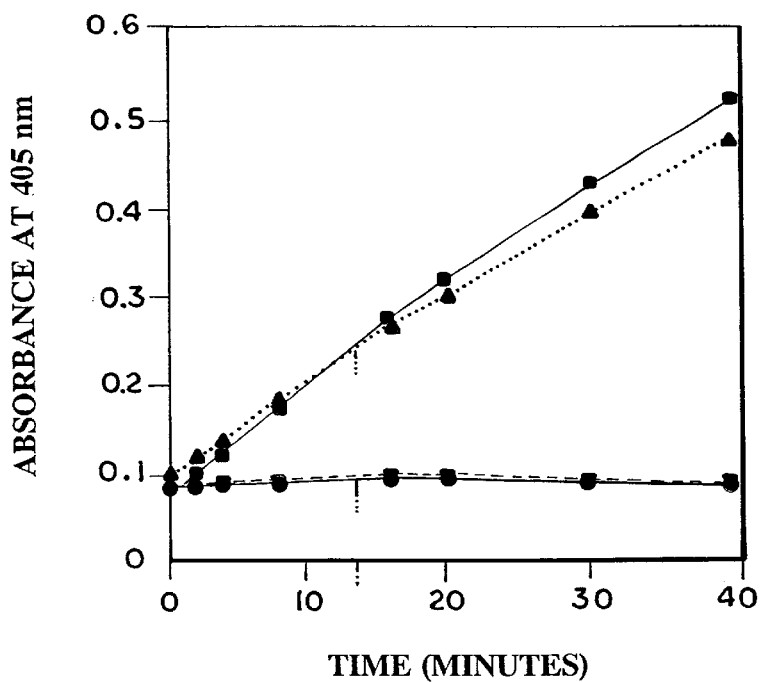
FIG. 11 is a graph showing the proteolytic activity of PSA using the synthetic substrate S-2586 (MeO-Suc-Arg-Pro-Tyr-NH-Np); the results are plotted as an increase in absorbance vs time in minutes. PSA (0.89 $\mu$M) (square) or ACT (0.92 $\mu$M) (circle) were incubated alone with substrate and hydrolysis measured over 40 min. For analysis of an inhibitory effect of ACT on PSA: PSA was preincubated with (inverted triangle) or without (regular triangle) equimolar amounts of ACT at 37° C. for 4 h prior to the addition of substrate. Upon addition of substrate, hydrolysis was measured over 40 min.

As shown in the figures, using equimolar concentrations of ACT and PSA, preincubation of PSA with ACT blocked both serine protease activity of purified PSA (FIG. 11) as well as the antimigratory effects of PSA on FGF-2-stimulated HUVEC (FIG. 12). Accordingly, these results demonstrate that the antiangiogenic properties of PSA are related to its serine protease activity.

SEQUENCE LISTING

<160> NUMBER OF SEQ ID NOS: 1

<210> SEQ ID NO 1
<211> LENGTH: 261
<212> TYPE: PRT
<213> ORGANISM: Homo sapiens

<400> SEQUENCE: 1

Met Trp Val Pro Val Val Phe Leu Thr Leu Ser Val Thr Trp Ile Gly
 1               5                   10                  15

```
Ala Ala Pro Leu Ile Leu Ser Arg Ile Val Gly Gly Trp Glu Cys Glu
            20              25              30

Lys His Ser Gln Pro Trp Gln Val Leu Val Ala Ser Arg Gly Arg Ala
        35              40              45

Val Cys Gly Gly Val Leu Val His Pro Gln Trp Val Leu Thr Ala Ala
    50              55              60

His Cys Ile Arg Asn Lys Ser Val Ile Leu Leu Gly Arg His Ser Leu
65              70              75              80

Phe His Pro Glu Asp Thr Gly Gln Val Phe Gln Val Ser His Ser Phe
            85              90              95

Pro His Pro Leu Tyr Asp Met Ser Leu Leu Lys Asn Arg Phe Leu Arg
            100             105             110

Pro Gly Asp Asp Ser Ser His Asp Leu Met Leu Leu Arg Leu Ser Glu
        115             120             125

Pro Ala Glu Leu Thr Asp Ala Val Lys Val Met Asp Leu Pro Thr Gln
    130             135             140

Glu Pro Ala Leu Gly Thr Thr Cys Tyr Ala Ser Gly Trp Gly Ser Ile
145             150             155             160

Glu Pro Glu Glu Phe Leu Thr Pro Lys Lys Leu Gln Cys Val Asp Leu
            165             170             175

His Val Ile Ser Asn Asp Val Cys Ala Gln Val His Pro Gln Lys Val
            180             185             190

Thr Lys Phe Met Leu Cys Ala Gly Arg Trp Thr Gly Gly Lys Ser Thr
        195             200             205

Cys Ser Gly Asp Ser Gly Gly Pro Leu Val Cys Asn Gly Val Leu Gln
    210             215             220

Gly Ile Thr Ser Trp Gly Ser Glu Pro Cys Ala Leu Pro Glu Arg Pro
225             230             235             240

Ser Leu Tyr Thr Lys Val Val His Tyr Arg Lys Trp Ile Lys Asp Thr
            245             250             255

Ile Val Ala Asn Pro
            260
```

REFERENCES

The following references are hereby incorporated by reference herein in their entirety.

Angiolillo, A. L., Sgadari, C., Taub, D. D., Liao, F., Farber, J. M., Miaheshwari, S., Kleinman, H. K., Reaman, G. H., and Tosato, G. (1995). Human interferon-inducible protein 10 is a potent inhibitor of angiogenesis in vivo. J. Exp. Med. 182, 155–162.

Cao, Y., Chen, C., Weatherbee, J. A., Tsang, M., and Folkman, J. (1995). Gro-beta, a C-X-C chemokine, is an angiogenesis inhibitor that suppresses the growth of Lewis lung carcinoma in mice. J. Exp. Med. 182, 2069–2077.

Chen, C., Parangi, S., Tolentino, M. J., and Folkman, J. (1995). A strategy to discover circulating angiogenesis inhibitors generated by human tumors. Cancer Res. 55, 4230–4233.

Clapp, C., Martial, J. A., Guzman, R. C., Rentier-Delrue, F., and Weiner, R. 1. (1993). The 16-kilodalton N-terminal fragment of human prolactin is a potent inhibitor of angiogenesis. Endocrinology 133, 1292–1299.

Colman et al. Hemostasis and Thrombosis, J. B. Lippincott Company, 2nd Edition p.20 (1987).

Dameron, K. M., Volpert, O. V., Tainsky, M. A., and Bouck, N. (1994). Control of angiogenesis in fibroblasts by p53 regulation of thrombospondin-1. Science 265, 1582.

Folkman, J. (1996). Tumor angiogenesis and tissue factor. Nature Med. 2, 167–168.

Folkrnan, J. (1989). What is the evidence that tumors are angiogenesis dependent?. J. Natl. Cancer Inst. 82, 4–6.

Folkman, J. (1985). Angiogenesis and its inhibitors. In Important Advances in Oncology 1985, V. T. DeVita, S. Hellman, and S. Rosenberg, eds. (Philadelphia: J. B. Lippincott Company), pp. 42–62.

Folkinan, J., Haundenschild, C. C., and Zetter, B. R. (1979). Long-term culture of capillary endothelial cells. Proc. Natl. Acad. Sci. USA 76, 5217–5221.

Gavrieli, Y., Sherman, Y., and Ben-Sasson, S. A. (1992). Identification of programmed cell death in situ via specific labeling of nuclear DNA fragmentation. J. Cell Biol. 119, 493–501.

Good, D. J., Polverini, P. J., Rastinejad, F., Le Beau, M. M., Lemons, R. S., Frazier, W. A., and Bouck, N. P. (1990). A tumor suppressor-dependent inhibitor of angiogenesis is immunologically and functionally indistinguishable from a fragment of thrombospondin. Proc. Nat. Acad. Sci. USA. 87, 6624–6628.

Grant, D. S., Tashiro, K.-l., Sequi-Real, B., Yamada, Y., Martin, G. R., and Kleinman, H. K. (1989). Two different laminin domains mediate the differentiation of human endothelial cells into capillary-like structures in vitro. Cell 58, 933–943.

Gross, J. L., Moscatelli, D., and Rifkin, D. B. (1983). Increased capillary endothelial cell protease activity in response to angiogenic stimuli in vitro. Proc. Natl. Acad. Sci. USA 80, 2623–2627.

Gupta, S. K., Hassel, T., and Singh, J. P. (1995). A potent inhibitor of endothelial cell proliferation is generated by proteolytic cleavage of the chemokine platelet factor 4. Proc. Natl. Acad. Sci. USA 92, 7799–7803.

Holmgren, L., O'Reilly, M. S., and Folkman, J. (1995). Dormancy of micrometastases: balanced proliferation and apoptosis in the presence of angiogenesis suppression. Nature Med. 1, 149–153.

Homandberg, G. A., Williams, J. E., Grant, D., B., S., and Eisenstein, R. (1985). Heparin-binding fragments of fibronectin are potent inhibitors of endothelial cell growth. Am. J. Path. 120, 327–332.

Hori, A., Sasada, R., Matsutani, E., Naito, K., Sakura, Y., Fujita, T., and Kozai, Y. (1991). Suppression of solid tumor growth by immunoneutralizing monoclonal antibody against human basic fibroblast growth factor. Cancer Res. 51, 6180–6184.

Kandel, J., Bossy-Wetzel, E., Radvany, F., Klagsburn, M., Folkman, J., and Hanahan, D. (1991). Neovascularization is associated with a switch to the export of bFGF in the multistep development of fibrosarcoma. Cell 66, 1095–1104.

Kim, K. J., Li, B., Winer, J., Armanini, M., Gillett, N., Phillips, H. S., and Ferrara, N. (1993). Inhibition of vascular endothelial growth factor-induced angiogenesis suppresses tumor growth in vivo. Nature 362, 841–844.

Maione, T. E., Gray, G. S., Petro, J., Hunt, A. J., Donner, A. L., Bauer, S. I., Carson, H. F., and Sharpe, R. J. (1990). Inhibition of angiogenesis by recombinant human platelet factor-4 and related peptides. Science 247, 77–79.

Millauer, B., Shawver, L. K., Plate, K. H., Risau, W., and Ullrich, A. (1994). Glioblastoma growth inhibited in vivo by a dominant-negative Flk-1 mutant. Nature 367, 576–579.

Muragaki, Y., Timmons, S., Griffith, C. M., Oh, S. P., Fadel, B., Quertemmous, T., and Olsen, B.-R. (1995). Mouse col18a1 is expressed in a tissue-specific manner as three alternative variants and is localized in basement membrane zones. Proc. Natl. Acad. Sci. USA 92, 8763–8767.

Nelson, J., Allen, W. E., Scott, W. N., Bailie, J. R., Walker, B., and McFerran, N. V. (1995). Murine epidermal growth factor (EGF) fragment (33–42) inhibits both EGF- and laminin-dependent endothelial cell motility and angiogenesis. Cancer Res. 55, 3772–3776.

Nguyen, M., Shing, Y., and Folkman, J. (1994). Quantitation of angiogenesis and antiangiogenesis in the chick embryo chorioallantoic e mbrane. Microvascular Res. 47, 31–40.

O'Reilly et al., 1997). Endostatin: An Endogeneous Inhibitor of Angiogenesis and Tumor Growth. Cell 88:277–285.

O'Reilly, M. S., Holmgren, L., Chen, C. C., and Folkman, J. (1996). ANGIOSTATIN™ induces and sustains dormancy of human primary tumors in mice. Nature Med. 2, 689–692.

O'Reilly, M. S., Holmgren, L., Shing, Y., Chen, C., Rosenthal, R. A., Moses, M., Lane, W. S., Cao, Y., Sage, E. H., and Folkman, J. (1994). ANGIOSTATIN™: A novel angiogenesis inhibitor that mediates the suppression of metastases by a Lewis lung carcinoma. Cell 79, 315–328.

O'Reilly, et al. "Angiogenic Regulation of Metastatic Growth" (1994). Cell, vol. 79 (2), Oct. 21, 1994. pp. 315–328.

Obeso, J., Weber, J., and Auerbach. R. (1990). A hemangioendothelioma-derived cell line: its use as a model for the study of endothelial cell biology. Lab. Invest. 63, 259–269.

Oh, S. K., Kamagata, Y., Muragaki, Y., Timmons, S., Ooshima, A., and Olsen, B. R. (1994). Isolation and sequencing of cDNAs for proteins with multiple domains of GlyXaa-Yaa repeats identify a distinct family of collagenous proteins. Proc. Natl. Acad. Sci. USA 91, 4229–4233.

Parangi, S., O'Reilly, M., Christofori, G., Holmgren, L., Grosfeld, J., Folkman, J., and Hanahan, D. (1996). Anti-angiogenic therapy of transgenic mice impairs de novo tumor growth. Proc. Natl. Acad. Sci. USA 93, 2002–2007.

Rastinejad, F., Polverini, P. J., and Bouck, N. P. (1989). Regulation of the activity of a new inhibitor of angiogenesis by a cancer suppressor gene. Cell 56, 345–355.

Rehn, M., and Pihlajaniemi, T. (1994). al(XVIII), a collagen chain with frequent interruptions in the collagenous sequence, a distinct tissue distribution, and homology with type XV collagen. Proc. Natl. Acad. Sci. USA 91, 4234–4238.

Rehn, M., and Pihlajaniemi, T. (1995). Identification of three N-terminal ends of type XVIII collagen chains and tissue-specific differences in the expression of the corresponding transcripts. J. Biol. Chem. 270, 4705–4711.

Riegman, P H J, Vlietstra, R J, Suurmeijer, L. (1992) Characterization of the human Kallikrein Locus. Genomics 14:6.

Sage, E. H., Bassuk, J. A., Vost, J. C., Folkman. M. J., and Lane, T. F. (1995). Inhibition of endothelial cell proliferation by SPARC is mediated through a Ca (2+)-binding EF-hand sequence. J. Cell Biochem. 57, 127–140.

Sakamato, N., Iwahana, M., Tanaka, N. G., and Osaka, 8. (1991). Inhibition of angiogenesis and tumor growth by a synthetic laminin peptide, CDPGYIGSR-$NH_2$. Cancer Res. 51, 903–906.

Shackleford, K. A., MacKellar, W. C., Habeck, L. L, Zimmerman, R. E., Richardson, J. M., Gygi, C. M. Sutkowski, D. M., Becker, G. W., Neubsuer, B. L., and Mendelsohn, L. G. (1997). Biochemical properties and cellular effects of prostate-specific antigen (PSA). Proceedings of the American Association for Cancer Research. 38 428.

Sokoll, L. J. and Chan D. W. (1997). Prostate-Specific Antigen Its Discovery and Biochemical Characteristics. Urologic Clinics of North America 24 253–259.

Strieter, R. M., Kunkel, S. L., Arenberg, D. A., Burdick, M. D., and Polverini, P. J. (1995). Human interferon-inducible protein 10 (IP-10), a member of the C-X-C chemokine family, is an inhibitor of angiogenesis. Biochem. Biophys. Res. Comm. 210, 51–57.

Studier, W. F., Rosenberg, A. H., Dunn, J. J., and Dudendorf, J. W. (1990). Use of T7 RNA polymerase to direct expression of cloned genes. Methods Enzymol. 85, 60–89.

Teicher, B. A., Holden, S. A., Ara, G., Sotomayor, E. A., and Dong, H. Z. (1994). Potentiation of cytotoxic cancer therapies by TNP-470 alone and with other antiangiogenic agents. Int. J. Cancer 57, 1–6.

Tolsma, S. S., Volpert, O. V., Good, D. J., Frazier, W. A., Polverini, P. J., and Bouck, N. (1993). Peptides derived from two separate domains of the matrix protein thrombospondin-1 have antiangiogenic activity. J. Cell Biol.122, 497–511.

Voest, E. E., Kenyon, B. M., O'Reilly, M. S., Truitt, G., D'Amato, R. J., and Folkman, J. (1995). Inhibition of angiogenesis in vivo by interleukin 12. J. Natl. Cancer Inst. 87, 581–586.

Yang N. (1992). Gene Transfer into Mammalian Somatic Cells in vivo, Crit. Rev. Biotechn. 12(4): 335–356.

We claim:

1. A method of regulating angiogenesis in an animal comprising administering to the animal an angiogenesis inhibiting amount of a composition comprising an anti-angiogenic cancer marker and a pharmaceutically acceptable excipient wherein the anti-angiogenic cancer marker is selected from the group consisting of PSA and carcinoembryonic antigen (CEA).

2. The method of claim 1 wherein the anti-angiogenic cancer marker is PSA.

3. The method of claim 1 wherein the anti-angiogenic cancer marker is CEA.

4. A method of regulating cell proliferation and/or migration in an animal comprising administering to the animal an inhibiting amount of a composition comprising an anti-angiogenic cancer marker and a pharmaceutically acceptable excipient wherein the anti-angiogenic cancer marker is selected from the group consisting of PSA and carcinoembryonic antigen (CEA).

5. The method of claim 4 wherein the anti-angiogenic cancer marker is PSA.

6. The method of claim 4 wherein the anti-angiogenic cancer marker is CEA.

* * * * *